US012185784B2

(12) United States Patent
Bowen

(10) Patent No.: US 12,185,784 B2
(45) Date of Patent: Jan. 7, 2025

(54) HEAD IMPACT RECOGNITION DEVICE

(71) Applicant: David Euan Murray Bowen, Edinburgh (GB)

(72) Inventor: David Euan Murray Bowen, Edinburgh (GB)

(*) Notice: Subject to any disclaimer, the term of this patent is extended or adjusted under 35 U.S.C. 154(b) by 371 days.

(21) Appl. No.: 17/607,376

(22) PCT Filed: Apr. 29, 2020

(86) PCT No.: PCT/GB2020/051045
§ 371 (c)(1),
(2) Date: Oct. 28, 2021

(87) PCT Pub. No.: WO2020/221999
PCT Pub. Date: Nov. 5, 2020

(65) Prior Publication Data
US 2022/0211135 A1    Jul. 7, 2022

(30) Foreign Application Priority Data
Apr. 29, 2019 (GB) .................................. 1905932

(51) Int. Cl.
*A42B 3/04*     (2006.01)
*A41D 13/00*    (2006.01)
(Continued)

(52) U.S. Cl.
CPC .......... *A42B 3/046* (2013.01); *A41D 13/0012* (2013.01); *A61B 5/103* (2013.01);
(Continued)

(58) Field of Classification Search
CPC ............................................. A63B 2243/0066
(Continued)

(56) References Cited

U.S. PATENT DOCUMENTS 6,065,158 A * 5/2000 Rush, III ............. A42B 3/0433
2/412
8,556,831 B1  10/2013 Faber et al.
(Continued)

FOREIGN PATENT DOCUMENTS

GB          2532237 A      5/2016

OTHER PUBLICATIONS

Great Britain Patent Application No. 1905932.8; Search Report; dated Oct. 29, 2019; 5 pages.
(Continued)

*Primary Examiner* — Jocelyn Bravo
(74) *Attorney, Agent, or Firm* — BAKER, HOSTETLER LLP

(57) ABSTRACT

The present disclosure provides sports apparatus including sports headwear and an impact detection arrangement for coupling to the sports headwear, e.g. a rugby scrum cap, to be worn by a user. The arrangement has a sensor for detecting an indication of an acceleration change experienced by the user's head when the sports headwear is being worn. The arrangement also has a visual indicator, e.g. an arrangement of LEDs, to provide a visual indication when the detected acceleration change exceeds a threshold. Advantageously, the present disclosure allows for immediate attention to be drawn to a player who has experienced a high g-force to their head, and therefore immediately alerts anyone in the vicinity that a medical check is needed to assess symptoms caused by the impact.

18 Claims, 15 Drawing Sheets

(51) Int. Cl.
*A61B 5/00* (2006.01)
*A61B 5/103* (2006.01)
*A63B 71/10* (2006.01)
*G01L 5/00* (2006.01)

(52) U.S. Cl.
CPC ............ *A61B 5/6803* (2013.01); *A63B 71/10* (2013.01); *G01L 5/0052* (2013.01); *A61B 2562/0219* (2013.01); *A63B 2220/53* (2013.01); *A63B 2243/0066* (2013.01)

(58) Field of Classification Search
USPC ..................................................... 2/410, 425
See application file for complete search history.

(56) References Cited

U.S. PATENT DOCUMENTS

| | | | | |
|---|---|---|---|---|
| 9,247,780 | B2* | 2/2016 | Iuliano | A42B 3/046 |
| 9,775,396 | B1 | 10/2017 | Olivares | |
| 9,795,177 | B1* | 10/2017 | Weaver | A42B 3/044 |
| 11,812,808 | B2* | 11/2023 | Morgan | A61B 5/11 |
| 2006/0038694 | A1 | 2/2006 | Naunheim et al. | |
| 2009/0307827 | A1* | 12/2009 | Aspray | G01P 15/036 |
| | | | | 73/514.01 |
| 2011/0219852 | A1* | 9/2011 | Kasten | G01L 5/0052 |
| | | | | 73/12.04 |
| 2012/0124720 | A1 | 5/2012 | Evans et al. | |
| 2013/0307678 | A1* | 11/2013 | Ransom | B62J 6/056 |
| | | | | 340/474 |
| 2014/0115759 | A1* | 5/2014 | Tomlin | A63B 69/002 |
| | | | | 340/689 |
| 2014/0143940 | A1* | 5/2014 | Iuliano | A42B 3/046 |
| | | | | 2/422 |
| 2014/0189928 | A1* | 7/2014 | Oleson | A61B 5/6804 |
| | | | | 600/388 |
| 2015/0109129 | A1* | 4/2015 | Merril | G08B 21/0438 |
| | | | | 702/141 |
| 2015/0196252 | A1* | 7/2015 | Iuliano | A61B 5/746 |
| | | | | 600/595 |
| 2017/0042272 | A1* | 2/2017 | Ferguson | A42B 3/121 |
| 2018/0007990 | A1* | 1/2018 | Olivares Velasco | ........... |
| | | | | G08B 21/0438 |
| 2018/0321097 | A1 | 11/2018 | Davis et al. | |
| 2021/0030097 | A1* | 2/2021 | Morgan | A61B 5/6803 |

OTHER PUBLICATIONS

International Patent Application No. PCT/GB2020/051045; Int'l Written Opinion and Search Report; dated Aug. 17, 2020; 12 pages.
International Patent Application No. PCT/GB2020/051045; Int'l Preliminary Report on Patentability; dated Nov. 11, 2021; 9 pages.

* cited by examiner (a)

(b)

HEAD IMPACT RECOGNITION DEVICE

The disclosure is the U.S. National Stage of International Application No. PCT/GB2020/051045, filed on Apr. 29, 2020, which claims the priority benefit of GB application No. 1905932.8, filed on Apr. 29, 2019. The entirety of the above-mentioned patent application is hereby incorporated by reference herein and made a part of this specification.

FIELD OF THE INVENTION

The present disclosure relates to detecting impacts received during sport, e.g. rugby. In particular, but not exclusively, the disclosure relates to sports apparatus including sports headwear and an impact detection arrangement for coupling to the sports headwear, e.g. protective headwear, to be worn by a user.

BACKGROUND

There is an increasing awareness of the risks of concussion in various different types of sporting activity, in particular high-contact sports such as rugby and gridiron football, but also other sports such as horse riding, cycling and skiing. A concussion may be regarded as a functional injury to the brain caused by a relatively large and fast change in acceleration of the head. In particular, this very quick change in movement causes the brain to press against the skull, resulting in injury. In rugby or gridiron football, such a rapid change in acceleration can often be caused by a player receiving or experiencing a high impact force to the head, neck or other part of their body, e.g. by being tackled by another player.

Second impact syndrome is a subsequent concussion being experienced prior to complete recovery from a previous concussion. In particular, second impact syndrome results from acute, serious brain swelling, which can cause vascular congestion and increased intracranial pressure that occurs rapidly, making it difficult to control. Second impact syndrome can result in serious, long-term brain damage, and can even be fatal.

Currently in sport, the effects of high impacts to a person's head are assessed by a referee or member of coaching staff based on the person's reaction or whether the referee or coaching staff recognise the person displaying any symptoms associated with concussion, such as amnesia, confusion, headache or loss of consciousness. Clearly, such an approach has the potential for a concussion to not be properly recognised or diagnosed, for example because the person receiving the high impact downplays symptoms they are experiencing or because symptoms are not properly recognised by other players, officials or coaching staff that are present. The consequences of a concussion not being properly diagnosed, such that the person is permitted to continue taking part in the sporting activity, are potentially severe, e.g. second impact syndrome.

It is against this background to which the present invention is set.

SUMMARY OF THE INVENTION

According to an aspect of the disclosure there is provided rugby apparatus comprising a rugby head guard arranged to receive a user's head, and a pocket receivable into a hole formed in the rugby head guard. The rugby apparatus includes an impact detection arrangement receivable into the pocket to couple the impact detection arrangement to the rugby head guard. The impact detection arrangement comprises a sensor configured to detect an indication of an acceleration change experienced by the user's head when the rugby head guard is being worn, a visual indicator configured to provide a visual indication when the detected acceleration change exceeds a threshold, and a housing arranged to house the sensor and the visual indicator. Such a housing, shell or casing provides protection for the components within. The hole may be formed—e.g. by drilling—an existing head guard, or the hole may be formed during manufacture of the head guard.

The impact received by the user can be, but need not be, an impact received directly to the user's head. For instance, the user may receive an impact to their neck or body, e.g. by being tackled by another player, which causes a sudden or rapid acceleration change of the user's head, specifically to their brain. That is, an impact to the player at any part of their body can cause the player's head to jolt.

By coupling the impact detection arrangement to the head guard, the arrangement is secured relative to the player's head so that movement of the player's head may be detected by the sensor. In particular, the arrangement or device acts as a recognition device of high-impact changes to the user's head area, mimicking the movement of the brain inside the skull. Specifically, by coupling the arrangement directly to the head, the arrangement can detect and relay the effects of directional changes that occur inside the skull of the user's brain. This direct coupling or attachment to the user's head provides a more accurate measurement of the head movement.

In the present disclosure, relatively high g-forces experienced by sports players, in particular rapid acceleration changes to a player's head or brain, are detected or recognised and then a warning that such an impact has been received is relayed visually to anyone in the vicinity of the player, e.g. team-mates, opponents, referees, coaches, spectators, etc. Advantageously, the present disclosure allows for immediate attention to be drawn to a player who has experienced a high g-force to their head, and therefore immediately alerts anyone in the vicinity that a medical check is needed to assess symptoms caused by the impact so that a determination may be made as to whether the player may continue partaking in the sporting activity. Specifically, provision of a visual indication, e.g. a light, that a high impact has occurred removes the uncertainty of attempting to identify when a player needs a medical check based solely on the player reporting the impact, or another person witnessing an impact and determining that the impact was sufficiently high to necessitate a medical check. A visual indication or cue that is visible to anyone in the vicinity of the player removes the risk of a player not reporting that they have experienced a high impact or of anyone else in the vicinity simply not witnessing a high impact. This means that players needing a medical check or medical attention may be easily identified, and reduces the chance of concussive symptoms being misdiagnosed or missed completely. This reduces the likelihood of a player suffering repetitive knocks or impacts, and so reduces the chances of a player suffering from an injury even more severe than concussion. Also, a visual cue visible to various people means that the responsibility of acting on a high-impact event then does not fall on a single person responsible for making an assessment as to whether medical attention is needed. In addition, the visual cue removes the risk of bias from the player receiving the impact, i.e. to downplay the level of the received impact. The invention provides a simple and easy to use arrangement that removes any uncertainty of how received impact data is to be used. That is, when the visual indication is activated then it is clear that a medical check is needed.

The arrangement is a wearable device that may be attached to, or incorporated into, an existing piece of equipment, i.e. head guard. The head guard may be a standard piece of equipment or designed specifically to incorporate the impact detection arrangement.

In some sports in which a player may receive relatively large impacts, the player wears a helmet formed of a solid, stiff (non-flexible) material, e.g. gridiron football. In contrast, in rugby such solid helmets are not permitted by regulation. Instead, protection in the form of a head guard is permitted; however, there are strict rules on how such a head guard is formed. In particular, a rugby head guard is formed from a relatively thin, soft material such as foam. As such, simply including an impact detection device in a rugby head guard (as may be possible in a solid helmet) without giving due consideration to ensuring the device will not be damaged upon impact or cause damage to the user or an opponent could be problematic. The present invention is advantageous in its provision of a protective pocket which is received into the head guard and into which the device can be securely inserted. The pocket offers a layer of protection between the user and the device, and also the device and an opponent. In particular, the pocket offers a padding element around the device with minimal effect to the wearer in a soft-shelled material so as to meet relevant (and relatively strict) guidelines and regulations.

The pocket may be formed from a material having a lower stiffness than the housing of the impact detection arrangement. The pocket may be formed from the same material as the rugby head guard. The pocket may be formed from a foam material.

The pocket may include a protective surrounding portion defining an aperture sized to receive and secure the impact detection arrangement therein. A depth of the surrounding portion may be greater than a depth of the housing of the impact detection arrangement. The pocket may include a flange portion extending from the protective surrounding portion. The flange may be attached to the rugby head gear.

The pocket may be attached to the rugby head gear by sewing. Conveniently, the pocket may be attached to the main body during manufacture of the head gear.

The housing may be formed from a flexible material. Conveniently, therefore, the arrangement may flex or mould in dependence on particular movements of the user's head and body to reduce the chance of the arrangement causing injury.

A part of the housing adjacent to the visual indicator may be formed from a transparent or translucent material. In particular, the visual indicator may be positioned adjacent such transparent material. Advantageously, this allows the visual indication, e.g. light, provided by the visual indicator to be visible by spectators, referees or other players.

The housing may be formed from thermoplastic polyurethane. This is a particularly suitable material for providing the necessary rigidity and flexibility required of the housing, and thereby guards against causing injury to the user or opponent during use.

The housing may have rounded edges. Optionally the housing is generally circular. Advantageously, this may result in a relatively compact arrangement. In the case of a rugby scrum cap, a generally circular arrangement comprising a circular housing may conveniently by received into a foam pocket of a padded part of the scrum cap. This results in a relatively discreet apparatus that does not alter the overall shape of bulk of the head wear to be worn by the player.

A depth of the housing may be less than a length and of a breadth of the housing. The housing may be generally planar.

The housing may include at least two component parts attached together by snap fitting to house the sensor and the visual indicator.

The image detection arrangement may include only a single printed circuit board. The sensor and the visual indicator may be arranged on the single printed circuit board. The sensor and the visual indicator may be arranged on the same side of the single printed circuit board.

The impact detection arrangement may include a battery arranged to power the visual indicator. The battery may be arranged on a side of the printed circuit board opposite to that of the sensor and the visual indicator. An interior of the housing includes a raised portion relative to an adjacent portion of the housing. The battery may abut the raised portion to secure the battery to the printed circuit board.

The visual indicator may comprise a light indicator. Optionally the light indicator comprises one or more LEDs. Advantageously, LEDs may have a relatively high-luminosity output, and therefore provide a clearer indication when a high impact has been received.

The hole may be positioned at a rear side of the rugby headguard. Optionally the hole is positioned away from a central part of the rugby head guard. Advantageously, positioning the arrangement in such a manner reduces the likelihood of a direct impact to the arrangement being received.

The rugby apparatus may comprise an outer cover element for attaching to the pocket and for covering an outer part of the hole of the rugby headguard. The outer cover element may be formed from a material through which the visual indicator is visible. The outer cover element may be formed from a material having a stiffness less than that of the housing of the impact detection apparatus.

The outer cover element may be formed from a fabric material, optionally a stretchable material, optionally Spandex. The outer cover element and/or pocket may be breathable. Advantageously, the outer cover element provides a barrier to protect the arrangement, for example from dirt or to provide water resistance. The outer cover element may be attached to the rugby headguard by sewing.

The rugby apparatus comprises a removable inner cover element for attaching to the pocket and for selectively covering or revealing an inner part of the hole of the rugby headguard. This allows relatively easy insertion and removal of the arrangement from the inner side of the head guard to, for example, inspect the arrangement after use. By providing access to the arrangement only on an inner side of the head guard, the arrangement cannot be removed—accidentally or otherwise—from the head guard while the user is wearing the head guard, i.e. when in use. The removable inner cover element may comprise hook and loop means for attaching to the pocket.

The impact detection arrangement may comprise an electrical switch for switching the impact detection arrangement between an operable state and an inoperable state. The rugby apparatus may comprise a magnetic device for operating the electrical switch, and the electrical switch may be arranged to change between the operable and inoperable states in response to the magnetic device being brought to within a threshold distance of the electrical switch.

The electrical switch may be arranged to change between the operable and inoperable states in response to the magnetic device being maintained within the threshold distance for less than a threshold time. The impact detection arrangement may be arranged to reset after the detected acceleration change exceeds the threshold acceleration change in response to the magnetic device being maintained within the threshold distance for greater than the threshold time.

It is specifically envisaged that the invention is applicable sports other than rugby. In particular, instead of the recited rugby apparatus and rugby head guard recited in the present aspect, the features outlined above—including the pocket and image detection arrangement, and any recited combination of the optional features—are equally compatible with more general sports apparatus including more general sports headwear. In particular, the sports headwear may be formed from a material less stiff than the housing of the impact detection arrangement, e.g. a soft shell head guard. A sports headband is one example of such sports headwear.

According to another aspect of the disclosure there is provided sports apparatus comprising sports headwear arranged to receive a user's head and a pocket receivable into a hole formed in the sports headwear. The apparatus includes an impact detection arrangement receivable into the pocket to couple the impact detection arrangement to the sports head wear. The impact detection arrangement comprises a sensor configured to detect an indication of an acceleration change experienced by the user's head when the sports headwear is being worn, a visual indicator configured to provide a visual indication when the detected acceleration change exceeds a threshold, and a housing arranged to house the sensor and the visual indicator. The sports headgear and the pocket may be formed from a material having a lower stiffness than the housing of the impact detection arrangement. The sports headwear may be any suitable headwear having a relatively soft shell, e.g. a sports headband, and is applicable to any sport in which such headwear may be worn.

According to another aspect of the disclosure there is provided an impact detection arrangement for coupling to a rugby head guard—or other sports headwear—to be worn by a user. The arrangement comprises a sensor configured to detect an indication of an acceleration change experienced by the user's head when the rugby head guard is being worn, a visual indicator configured to provide a visual indication when the detected acceleration change exceeds a threshold, and a housing arranged to house the sensor and the visual indicator. The sensor and the visual indicator may be arranged on a single printed circuit board of the impact detection arrangement.

According to an example of the disclosure there is provided an impact detection arrangement. The arrangement is for coupling to sports headwear that is to be worn by a user or player. The arrangement comprises a sensor configured to detect an indication of an acceleration change experienced by the user's head when the sports headwear is being worn. In particular, the sensor is configured to receive data indicative of the acceleration change experienced by the user's head. The arrangement also comprises a visual indicator configured to provide a visual indication when the detected acceleration change exceeds a threshold change value. The sensor may comprise an accelerometer.

The sensor may comprise a gyroscope.

It is specifically envisaged that the image detection arrangement may equally be inserted into more general sports headwear, particularly sports headwear formed from a material less stiff than the housing of the impact detection arrangement, e.g. a soft-shell head guard. A sports headband is one example of such sports headwear and may be used in any suitable sport, e.g. association football or field hockey. However, it is also envisaged that the image detection arrangement could alternatively be inserted into a helmet, i.e. solid- or hard-shell headwear, to be used in sports where such headwear is used, e.g. a helmet used in gridiron football.

The visual indicator may be arranged atop the sensor, or generally adjacent to the sensor.

The sensor may be positioned on a first substrate, e.g. a printable circuit board. The visual indicator may be positioned on a second substrate separate from the first substrate. There may be an electrical connection between the first and second substrates. In particular, opening or closing of a switch on the first substrate may cause activation or deactivation of the visual indicator, e.g. to cause the LEDs to light up or switch off. Power to such an electrical circuit may be provided by a battery on the first substrate, e.g. a coin battery.

The threshold may be user-adjustable. The relevant threshold, i.e. the impact level at which a player or user needs to receive a medical check, may vary for different ages, levels and/or sports. Advantageously, a user-adjustable threshold provides flexibility of use between different sports and individuals.

The threshold change value may be a first threshold change value greater than a second threshold change value. The visual indicator may be configured to provide the visual indication when the detected acceleration change exceeds the second threshold change value a predetermined number of times greater than one. Advantageously, consecutive, smaller impacts may therefore be recognised.

The housing may be generally elongate. The housing may be shaped to conform to a curvature of the user's head.

The housing may comprise a first housing part, or sensor housing part, arranged to house the sensor. The housing may comprise a second housing part, or visual indicator housing part, arranged to house the visual indicator.

Conveniently, the sensor housing part may be arranged in use at, or adjacent to, a rear side of the user's neck. Advantageously, this is an area of the user's body that is less likely to receive direct impacts during certain sports, e.g. rugby, while positioning the sensor housing part here may still allow relatively easy connection to the head gear.

The arrangement may comprise a locking mechanism arranged to connect the first and second housing parts together. Conveniently, the first (sensor) housing part may be disconnected from the rest of the arrangement to, for example, reset the sensor or adjust the threshold while the rest of the arrangement may remain in situ coupled to the head gear.

The sensor may be configured to receive data indicative of the acceleration change experienced by the user's head. The arrangement may comprise a wireless transmitter configured to transmit the received acceleration data off-board the arrangement. The acceleration data may be transmitted to a mobile device, optionally in real time. Advantageously, by providing such data to a mobile or handheld device a relatively large amount of data may be collected and used to identify and track head impact levels throughout the duration an entire sporting contest. In turn, this may lead to improved diagnosis from medical staff, either on the sidelines or elsewhere, who may not have witnessed a particular incident involving an impact.

According to another example of the disclosure there is provided sports headwear comprising a main body arranged to receive a user's head, and a pocket coupled to the main body and arranged to receive the impact detection arrangement described above. The impact detection arrangement is therefore coupled to the sports headwear. In this way, the impact detection arrangement can track and detect g-forces experienced by a user's head, in particular their brain, to determine whether a brain injury, e.g. concussion, may have occurred as a result of a high impact to the player or user.

The pocket may be positioned centrally on the main body of the head guard, i.e. centrally relative to the user's head. Such positioning may provide more accurate measurements for impacts received on either side of the user, i.e. either side of the user's head or body. The sleeve may include a strap or belt that further secures the pocket to the main body of the head guard. In particular, the strap may extend from a lower end to upper end of the pocket, and may be wrapped around the head guard to further secure or fasten the arrangement to the head guard. For instance, the strap may be secured by means of a hook-and-loop attachment, e.g. Velcro®.

The pocket may be integrally formed with the main body.

The sports headwear may be a rugby head guard or scrum cap.

According to another example of the disclosure there is provided apparatus for sports impact detection. The apparatus comprises the impact detection arrangement described above. The apparatus comprises the sports headwear described above. The sports headwear is arranged to be worn on a user's head and the impact detection arrangement is arranged to be coupled to the sports headwear to detect acceleration change experienced by the user's head upon the user receiving an impact.

According to another example of the disclosure there is provided an impact detection method. The method comprises providing an impact detection arrangement for coupling to sports headwear to be worn by a user. The arrangement has a sensor and a visual indicator. The method comprises detecting, using the sensor, an indication of an acceleration change experienced by the user's head when the sports headwear is being worn. The method comprises providing a visual indication using the visual indicator when the detected acceleration change exceeds a threshold change value.

BRIEF DESCRIPTION OF THE DRAWINGS

Examples of the disclosure will now be described, by way of example only, with reference to the accompanying drawings, in which.

DETAILED DESCRIPTION

Figure 1:
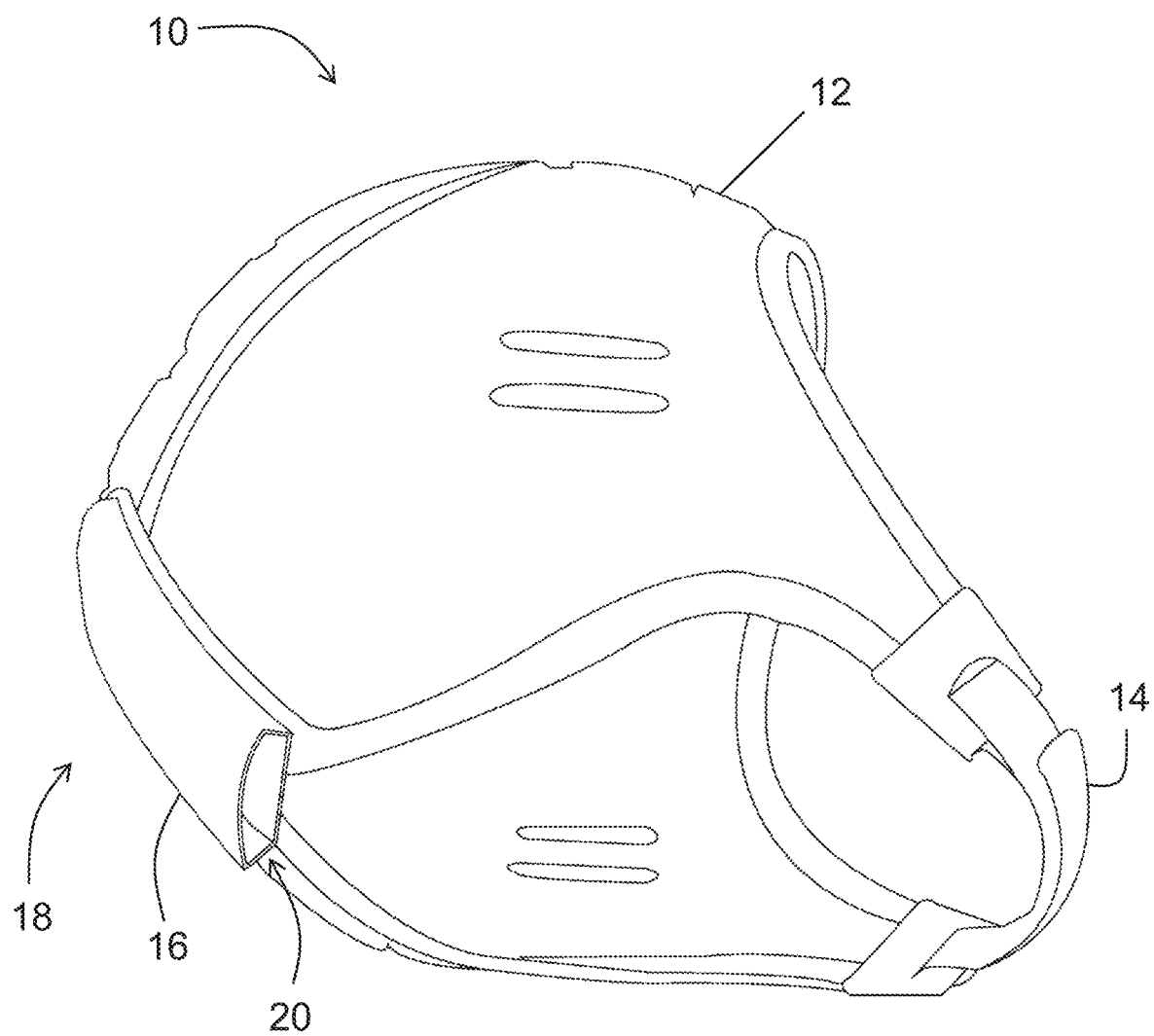
FIG. 1 shows a schematic view of a rugby head guard having a pocket.

FIG. 1 schematically illustrates sports headwear in the form of a rugby head guard 10, also referred to as a scrum cap, in accordance with an example of the disclosure. Scrum caps are commonly worn by rugby players to protect their ears, in particular to protect their ears when contesting a scrum. Typically, the head guard is formed from soft, thin material such as foam. The head guard 10 has a main body 12 for receiving the head of a player or user, and straps 14 attached to the main body 12 that may be secured together when the user is wearing the head guard 10 to secure the head guard 10 to the user. In particular, the straps 14 may be secured together under or around the user's chin or jaw.

The head guard 10 includes a pocket 16 at a rear side 18 of the head guard 10. The pocket 16 is in the form of an elongate slot that has a pocket opening 20 at a lower side 22 of the head guard 10 and which faces in a generally downwards direction (when worn by a standing user). The pocket 16 is integral with the main body 12 of the head guard 10, and the pocket 16 is attached to, or formed with, the main body 12 during manufacture of the head guard 10. For instance, the pocket 16 may be sewn onto the main body 12 during manufacture of the head guard 10. The pocket 16 is arranged to receive therein an impact detection arrangement (not shown), as is discussed in detail below.

Figure 2:
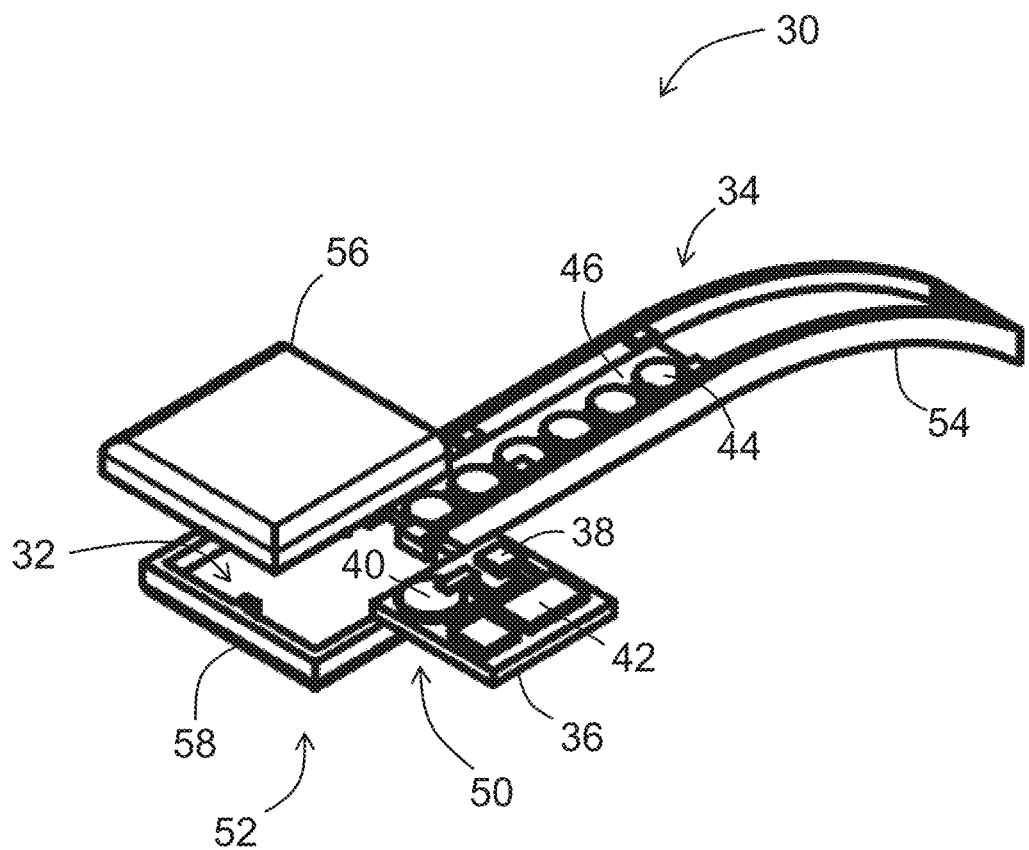
FIG. 2 shows a schematic view of an impact detection arrangement for being received in the pocket of FIG. 1.
Figure 3:
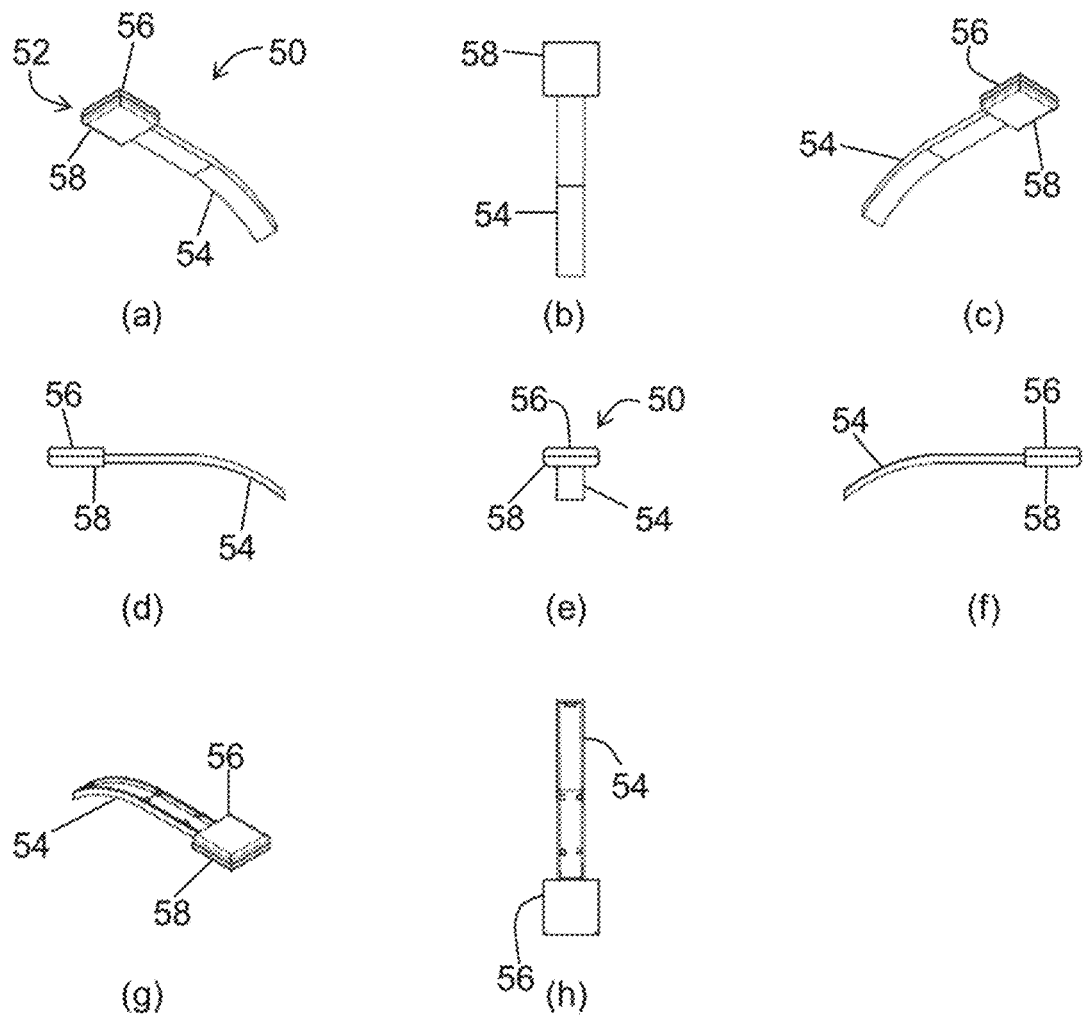
FIGS. 3(a)-3(h) show perspective views of a housing of the impact detection arrangement of FIG. 2.
Figure 4:
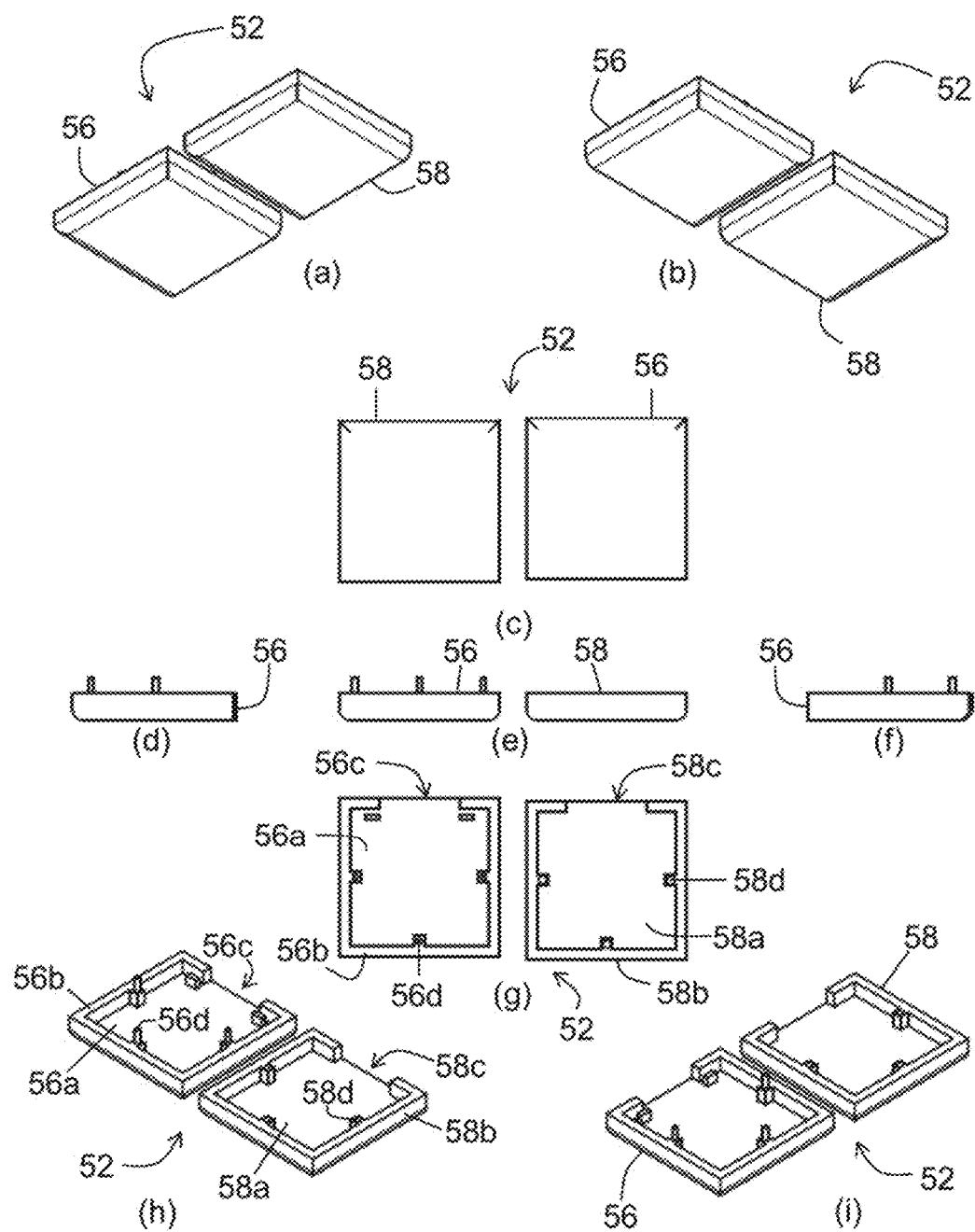
FIGS. 4(a)-4(i) show perspective views of a first housing section of the housing of FIGS. 3(a)-3(f)
Figure 5:
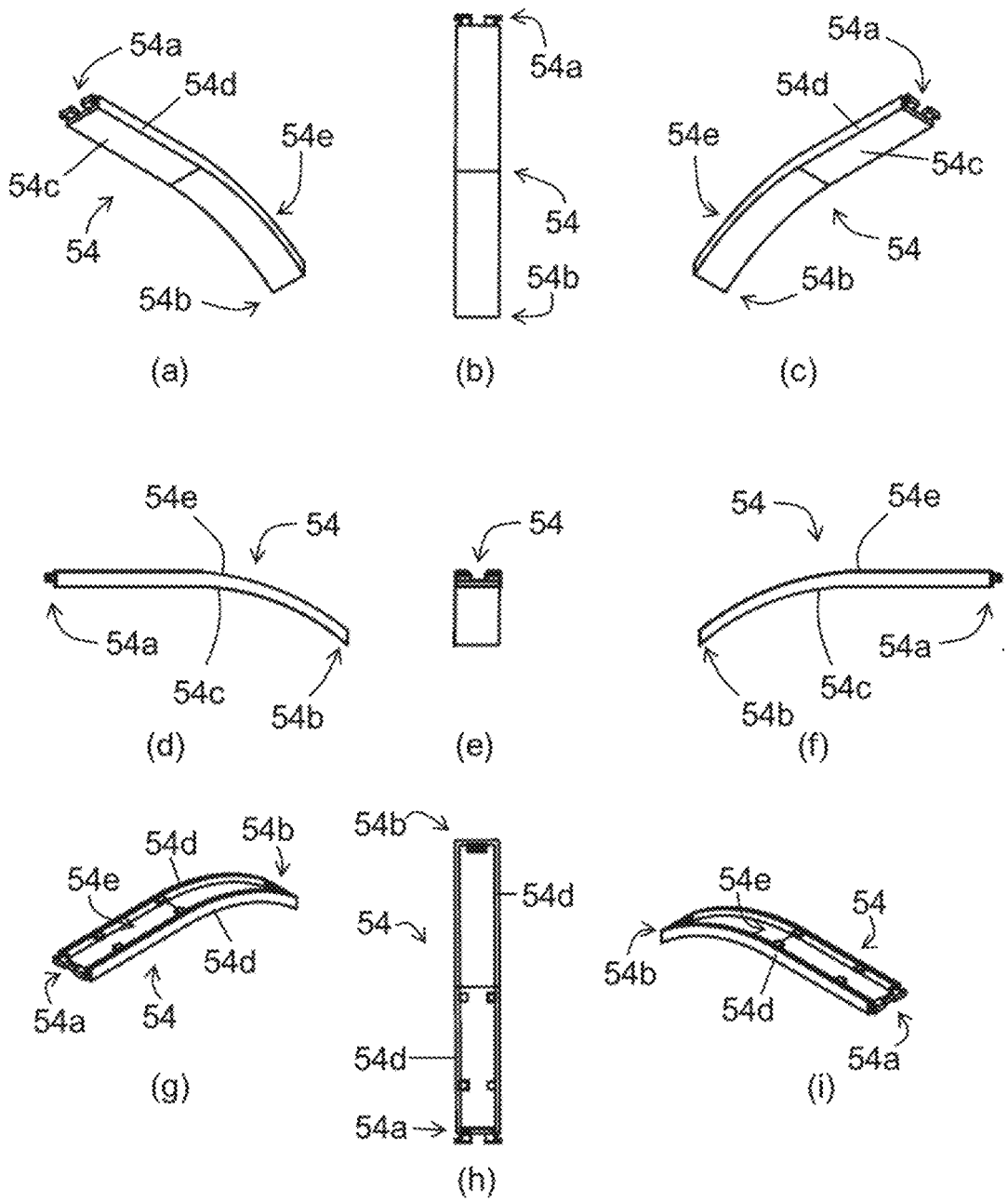
FIGS. 5(a)-5(i) show perspective views of a second housing section of the housing of FIGS. 3(a)-3(f)

FIG. 2 schematically illustrates an example of an impact detection arrangement 30 that may be inserted into the pocket 16 of the head guard 10 (shown in FIG. 1). In particular, the arrangement 30 is for detecting impacts received by a user that is wearing the head guard 10 when playing rugby. Specifically, the arrangement 30 is for detecting high impacts received by the user, e.g. when the user is tackled by an opponent, and for alerting other people in the vicinity when a received impact is greater than a threshold level.

The arrangement 30 includes a sensor section 32 and a lighting section 34 adjacent to the sensor section 32. The sensor section 32 may also be referred to as the first section 32, and the lighting section 34 may also be referred to as the second section 34. The sensor section 32 includes a printable circuit board 36, or microchip or substrate, having a sensor 38 in the form of an accelerometer and gyroscope. The circuit board 36 also has a battery source in the form of a coin battery 40, also referred to as a button cell. The battery 40 is connected to, and provides electrical power to, the sensor 38. The circuit board 36 also has a wireless radio transmitter 42. The lighting section 34 includes a visual indicator in the form of a plurality of light emitting diodes (LEDs) 44. In particular, the lighting section 34 includes a row of five, mutually adjacent LEDs 44. Each of the LEDs 44 is located on a respective circuit board 46. The battery 40 is also connected to the LEDs 44 to provide electrical power to the LEDs 44.

The arrangement 30 includes a casing or housing 50 for housing the circuit boards 36, 46. With continued reference to FIG. 2, and additional reference to FIGS. 3(a)-3(h)—which show various views of the housing 50—the housing 50 includes a sensor housing part 52, also referred to as a first housing part 52, defining the first section 32 and a light housing part 54, also referred to as a second housing part 54, defining the second section 34, where the sensor and light housing parts 52, 54 are connected together.

The housing 50 is formed from a material that protects the components it houses therein, i.e. the circuit boards 36, 46, but is also flexible. In the described example, the housing 50 is formed from thermoplastic polyurethane.

With continued reference to FIG. 2 and FIGS. 3(a)-3(h), and additional reference to FIGS. 4(a)-4(i)—which show various views of the sensor housing part 52—the sensor housing part 52 has an upper part 56 and a lower part 58. Each of the upper and lower parts 56, 58 is of generally rectangular shape and are brought together to form a generally cuboidal first section 32. Each of the upper and lower parts 56, 58 has a respective base cover 56a, 58a and side walls 56b, 58b extending around the perimeter of the base covers 56a, 58a. The side walls 56b, 58b each are discontinuous along one side of the respective base covers 56a, 58a to form a gap or space 56c, 58c in the walls 56b, 58b. When the upper and lower parts 56, 58 are brought together to form the sensor housing part 52 the gaps 56c, 58c are aligned to form an aperture. The upper and lower parts 56, 58 have respective connectors 56d, 58d for joining or connecting the upper and lower parts 56, 58 together. In particular, the upper part 56 has a male connector 56d at each side thereof, which is to be inserted into a respective female connector 58d of the lower part 58 so as to connect the upper and lower parts together 56, 58.

Purely by way of example, various dimensions of the sensor housing part 52 may be as follows. The sensor housing part 52 may be generally square having sides of approximately 30 mm. The depth of each of the upper and lower parts 56, 58 may be approximately 5 mm. The male connectors 56d may be approximately 3 mm in length and approximately 1 mm wide. It will be understood that any appropriate dimensions may be used.

With continued reference to FIG. 2 and FIGS. 3(a)-3(h), and additional reference to FIGS. 5(a)-5(i)—which show various views of the light housing part 54—the light housing part 54 is elongate and, in use, extends from a lower part to an upper part of a user's head at the rear of the user's head. In particular, the light housing part 54 is curved or shaped to conform to a curvature of the user's head, specifically the rear side of the head. The light housing part 54 may extend in a straight or linear manner from a lower end 54a and then curve to conform to the curvature of the user's head towards an upper end 54b of the light housing part 54. In the described example, the light housing part 54 is curved from approximately half way along the light housing part 54 to its upper end 54b, although any appropriate variant is envisaged.

Along the length of the light housing part 54, a rear part 54c and side parts 54d of the light housing part 54 are formed from the flexible material, e.g. thermoplastic polyurethane, mentioned above. A front part 54e opposite the rear part 54c is formed from a transparent material. When the LEDs 44 are positioned in the light housing part 54 they are arranged to face outwardly towards the front part 54e of the light housing part 54, and the transparent material of the front part 54e allows light from the LEDs 44 to be visible outside of the light housing part 54. The transparent material may be thermoplastic polyurethane.

The light housing part 54 includes a locking mechanism 54f at its lower end 54a in the form of resilient clips 54f. The clips 54f are arranged to be received into the aperture formed by the gaps 56c, 58c in the sensor housing part 52. In particular, the clips 54f engage with the sensor housing part 52 to secure or lock the light housing part 54 to the sensor housing part 52. The resiliency of the clips means that the light housing part 54 can conveniently be engaged and disengaged from the sensor housing part 52 as desired.

Purely by way of example, various dimensions of the light housing part 54 may be as follows. The light housing part 54 may be approximately 100 mm in length, approximately 15 mm in width, and approximately 5 mm in depth. The side parts 54d may be approximately 1.5 mm in width. Each of the clips 54e may be approximately 5 mm in width. It will be understood that any appropriate dimensions may be used.

Figure 6:
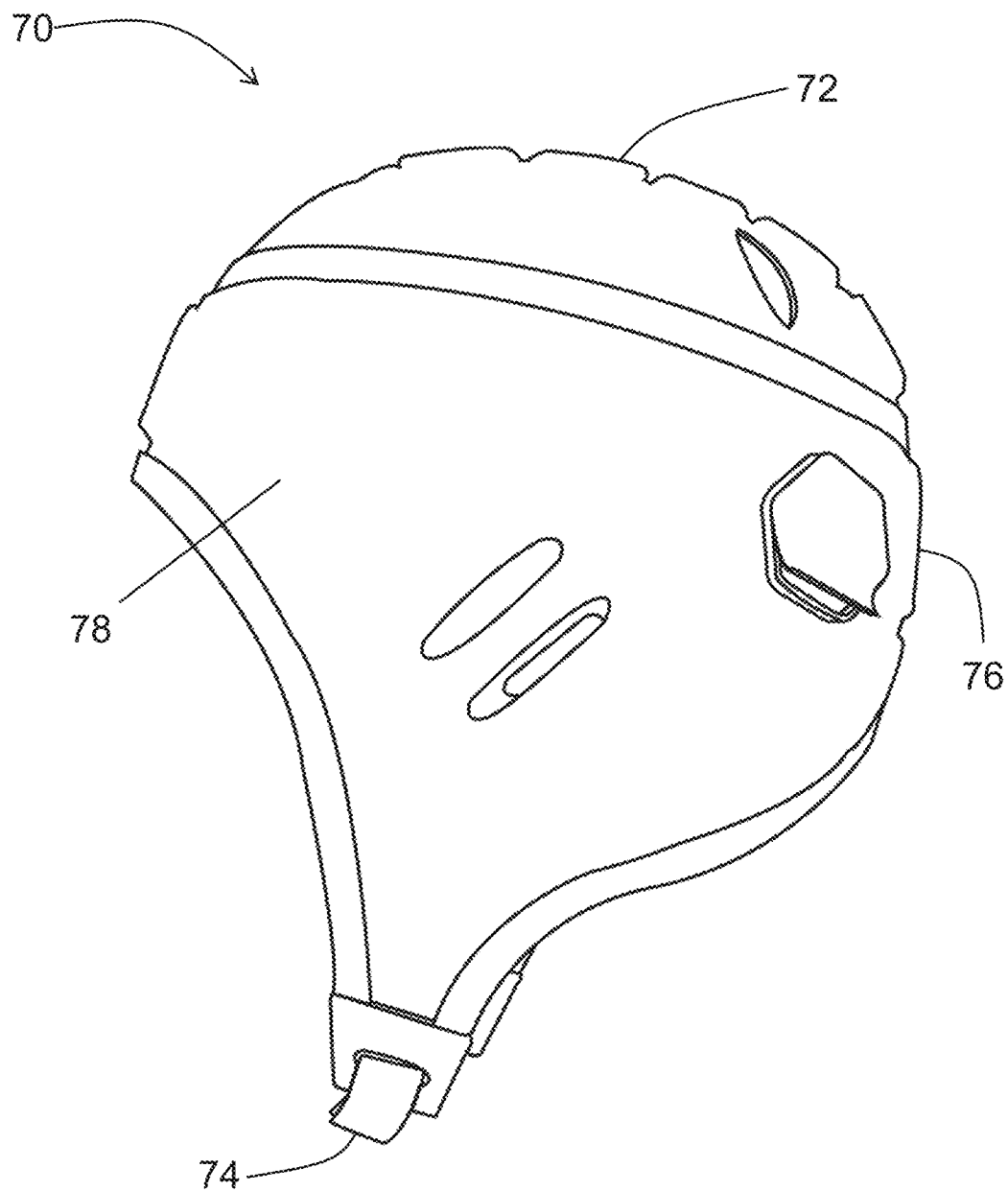
FIG. 6 shows a schematic view of a rugby head guard having a pocket.

FIG. 6 schematically illustrates sports headwear in the form of a rugby head guard 70 in accordance with another example of the disclosure. Similarly to the previous example, the head guard 70 includes a main body 72 and straps 74. The main body 72 is again formed from soft, thin material such as foam. Also similarly to the previous example, the head guard 70 includes a pocket 76; however, unlike in the previous example, the pocket 76 is of generally circular shape. The pocket 76 is integral with the main body 72 of the head guard 70, and the pocket 76 is formed with the main body 72 during manufacture of the head guard 70. As seen in FIG. 6, the main body 72 of the head guard 70 has a design formed by spaced apart, shaped padded parts 78. In the described example, the padded parts 78 are generally octagonal in shape; however, any appropriate shape, or mix of shapes may be used, e.g. triangles, rectangles, square, pentagons, hexagons, heptagons, nonagons, decagons, etc. In the described example, the pocket 76 is of substantially the same size as one of the shaped padded parts 78 and is located where one (or more) of the padded parts 78 would otherwise be.

Figure 7:
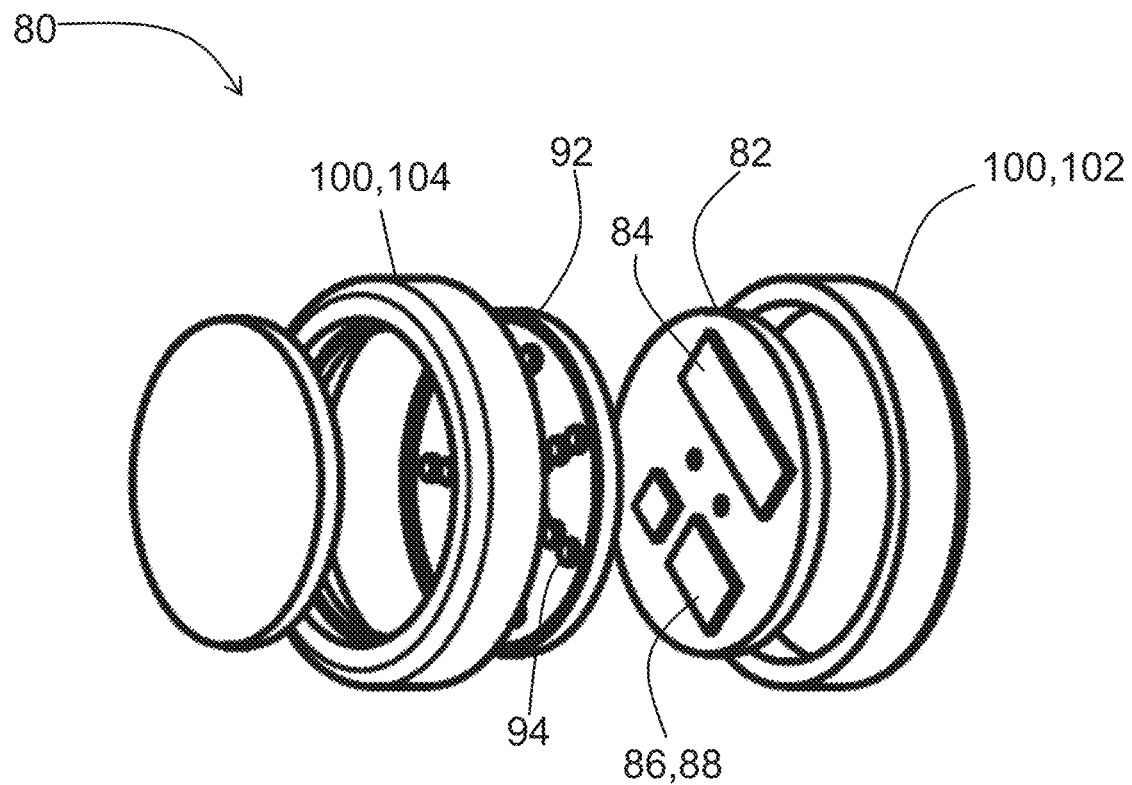
FIG. 7 shows a perspective view of an impact detection arrangement for being received in the pocket of FIG. 6.
Figure 8:
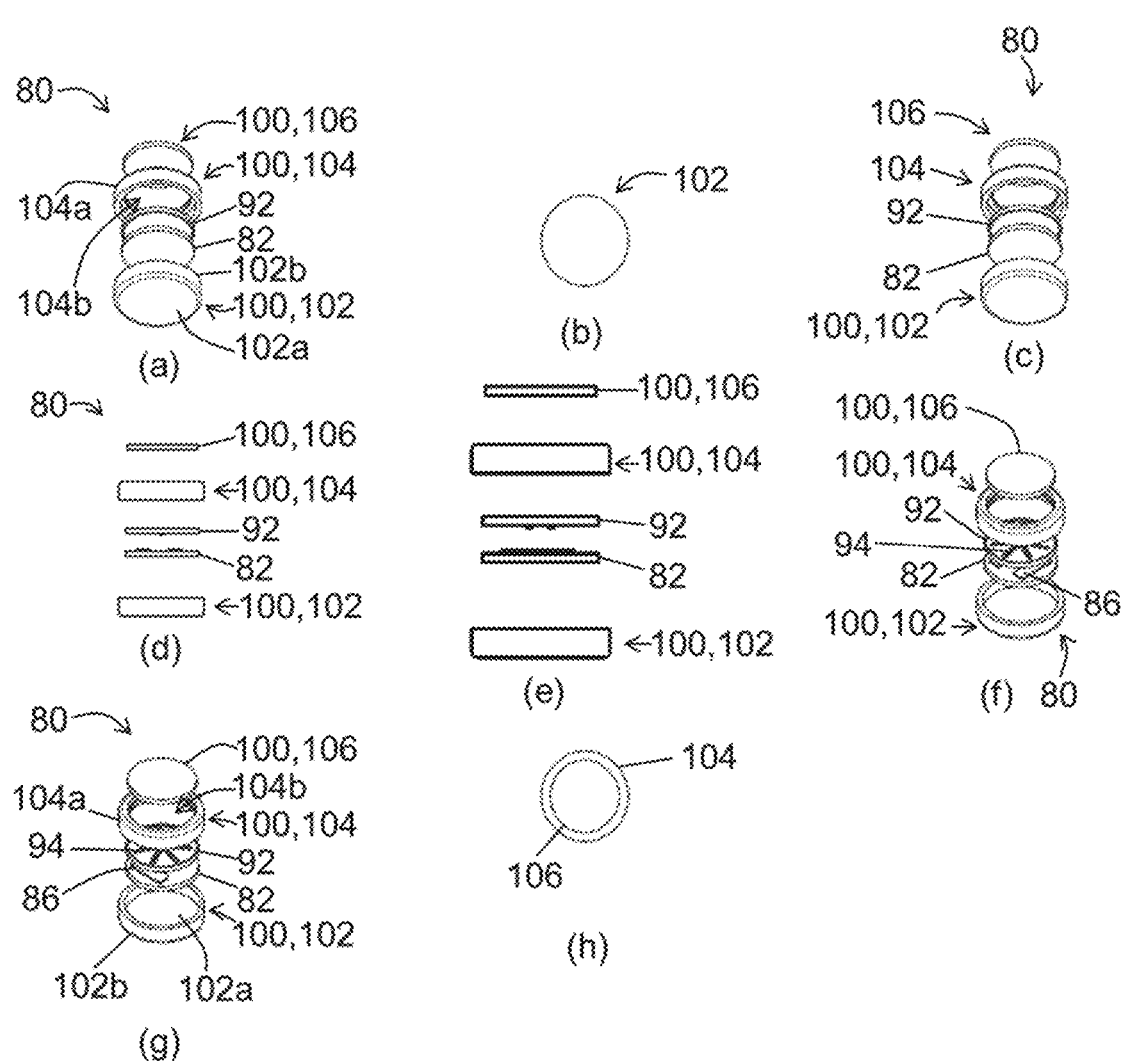
FIGS. 8(a)-8(h) show further perspective views of the impact detection arrangement of FIG. 7.

FIG. 7 schematically illustrates an exploded view of an impact detection arrangement 80 in accordance with another example of the disclosure, where the arrangement 80 may be inserted or received into the pocket 76 of the head guard 70 (shown in FIG. 6). The arrangement 80 is generally circular and the pocket 76 is sized to receive the arrangement 80. That is, the arrangement 80 may be embedded within the head guard 70. Note that in different examples the arrangement 80 and pocket 76 may be of any suitable shape.

As for the arrangement 30 of the previous example, the arrangement 80 is for detecting impacts received by a user that is wearing the head guard 70 when playing sport, in particular rugby. Specifically, the arrangement 80 is for detecting high impacts received by the user, and for alerting other people in the vicinity when a received impact is greater than a threshold level.

With continued reference to FIG. 7, and additional reference to FIGS. 8(a)-8(h)—which show exploded views of the arrangement 80—the arrangement 80 includes a printable (sensor) circuit board 82, or microchip or substrate, having a sensor 84 in the form of an accelerometer and gyroscope. The circuit board 82 also has a battery source in the form of a coin battery 86. The circuit board 82 also has a wireless radio transmitter 88. The arrangement 80 also includes another (lighting) substrate or circuit board 92 having a visual indicator in the form of a plurality of LEDs 94. In the described example, the LEDs 94 are arranged to form a pattern in the form of a number of spokes emanating from a centre to an edge of the substrate 92; however, any suitable pattern of LEDs may be created.

The arrangement 80 also includes a casing or housing, generally referred to using reference numeral 100, for housing the circuit boards 82, 92. The housing 100 includes a base housing part 102, a ring housing part 104, and a housing cover part 106. As in the previously-described example, the housing 100 is formed from a flexible material, in particular thermoplastic polyurethane. The base housing part 102 has a base 102a and a rim 102b. The sensor circuit board 82 is received into the base housing part 102 so that it is adjacent to the base 102a and surrounded by the rim 102b. The lighting circuit board 92 may then be received into the base housing part 102 so that it is adjacent to, in particular atop, the sensor circuit board 82 and also surrounded by the rim 102b. The ring housing part 104 may then be placed on the base housing part 102 to encase or encapsulate the sensor and lighting substrates 82, 92. In particular, a rim 104a of the ring housing part 104 overlies the base housing part rim 102b. Note that the ring housing part 104 has an opening 104b at its top. The housing cover part 106 is transparent and is sized to be received into, and secured relative to, the opening 104b of the ring housing part 104. When the housing 100 is assembled, the LEDs 94 are visible through the transparent housing cover part 106.

Purely by way of example, the diameter of the base housing part 102 may be approximately 25 mm, the diameter of the sensor and lighting substrates or circuit boards 82, 92 may be approximately 21 mm, and the diameter of the transparent housing cover part 106 may be approximately 20 mm. It will be understood that any appropriate dimensions may be used.

Figure 9:
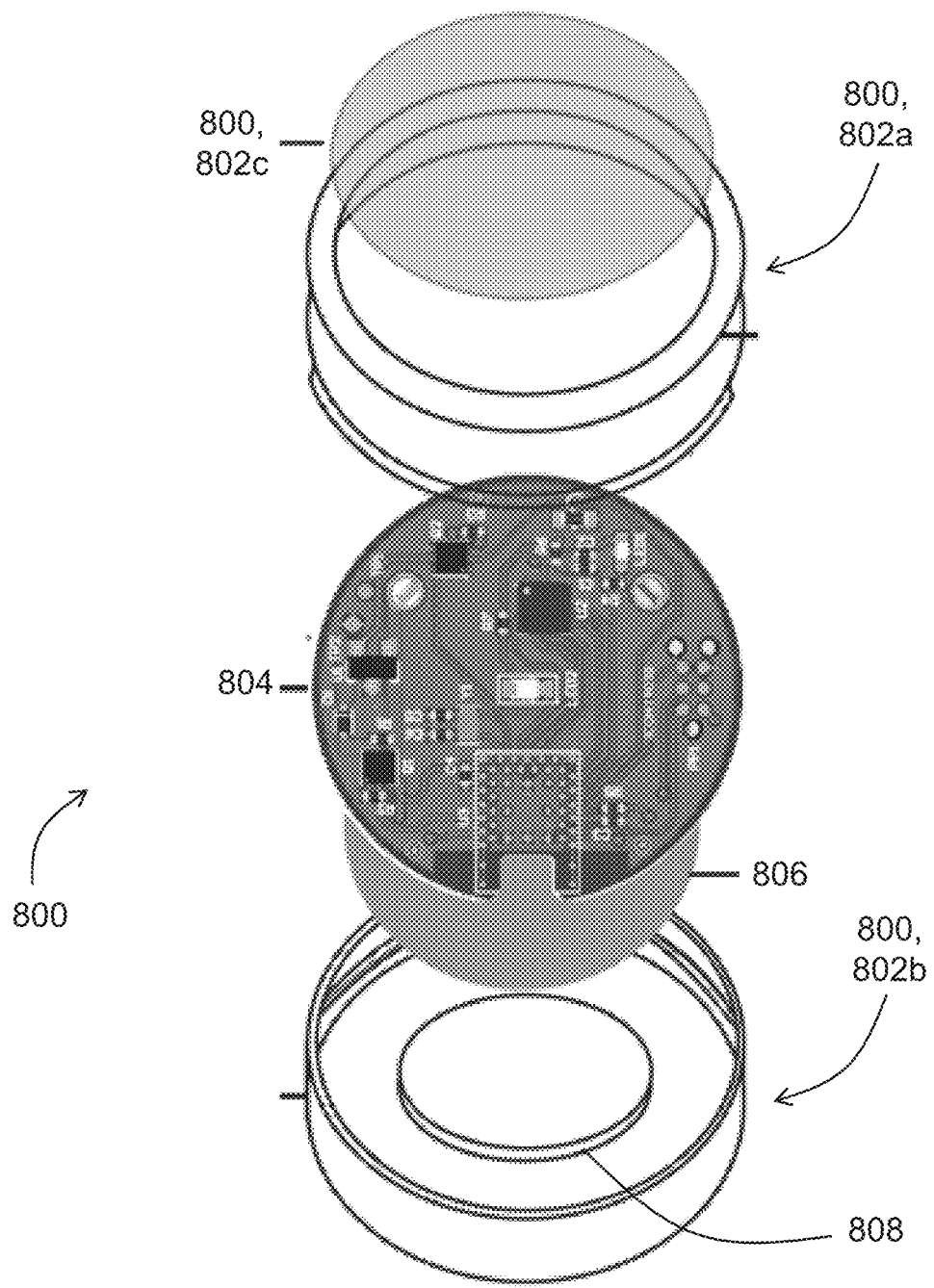
FIG. 9 shows a perspective view of another impact detection arrangement.

FIG. 9 shows a perspective view of an impact detection arrangement 800 similar to the impact detection arrangement 80. The arrangement 800 includes a housing 802—also referred to as a casing or shell—including an upper part 802a, a lower part 802b and a transparent screen or portion 802c. The arrangement 800 also includes a single printed circuit board 804—also referred to as a substrate—and a battery 806 in the form of a coin cell.

An interior of the lower part 802b of the housing 800 has a raised portion 808. As indicated in FIG. 9, the battery 806 is positioned between the lower part 802b of the housing 802 and a rear side of the substrate 804. When the arrangement 800 is assembled the raised portion abuts the battery 806 and presses it into the substrate 804 to secure it in place. The electrical components other than the battery 804 are arranged on the upper side of the substrate, i.e. the side opposite to the battery 806, and will be discussed in greater detail below. It is seen that a depth of the housing 802 is less than a length of and a breadth of the housing 802, and that the housing is generally planar. This allows the arrangement to fit neatly and unobtrusively into a rugby head guard, which is formed of relatively thin, soft material.

Figure 10:
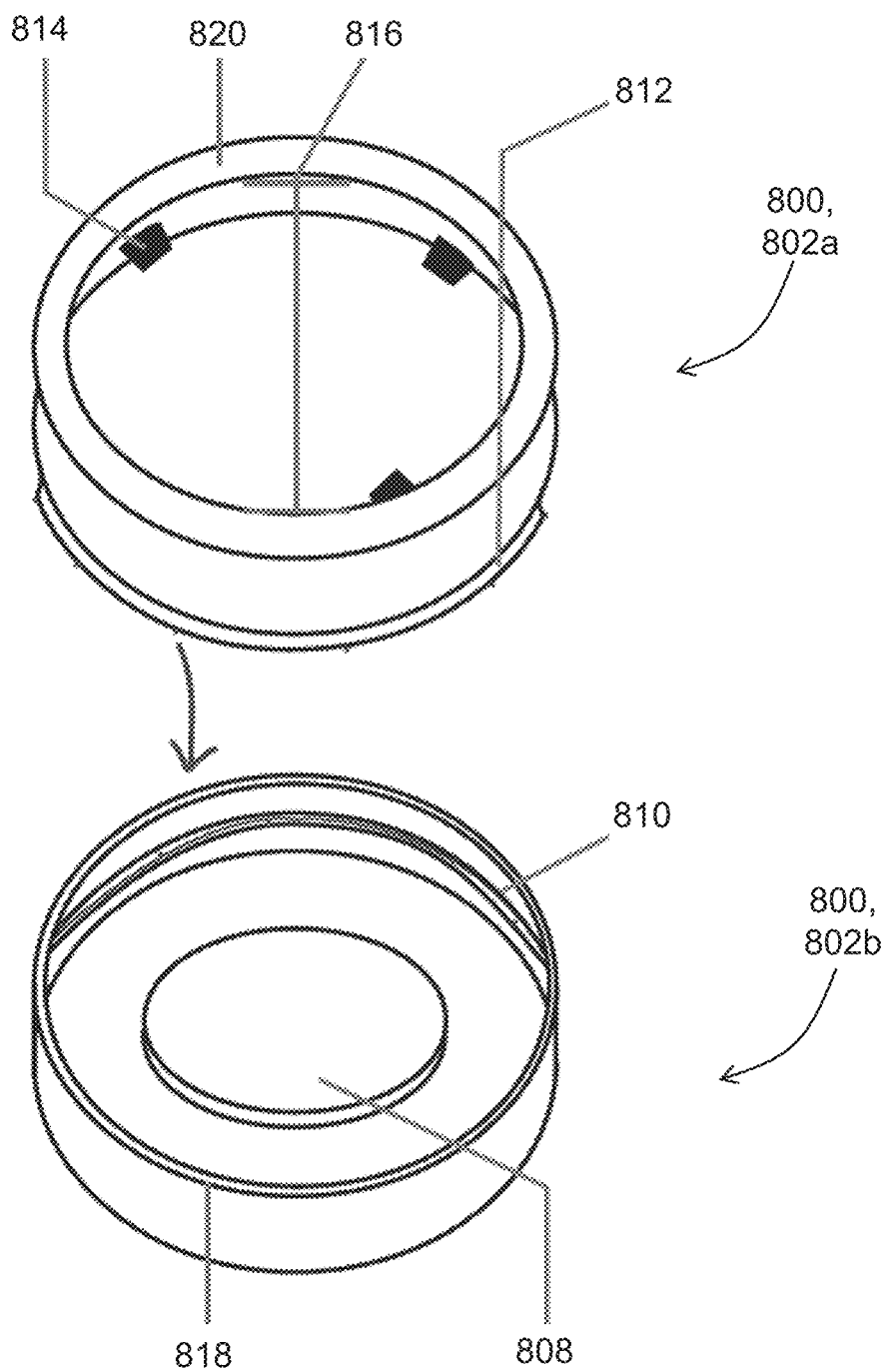
FIG. 10 shows a housing of the impact detection arrangement of FIG. 9.

FIG. 10 shows the upper and lower parts 802a, 802b of the housing 802 in greater detail. The lower part 802b has an indent or female part 810 around the inside thereof for receiving a male counterpart or ridge 812 on the outside of the upper part 802a in the form of a seal clip ring that flares to attach the upper and lower parts 802a, 802b together. This allows the upper and lower parts 802a, 802b to be secured together using a snap fit which advantageously obviates the need for additional attaching parts. The inside of the upper casing 802a includes a number of clips 814 disposed therein to receive and fasten the substrate 804 securely in place in the housing 800. A top side of the upper part 802a is open and defines an aperture 816 to allow the transparent cover 802c to be positioned therein. A rim 818 of the lower part 802b may be slightly narrower than a rim 820 of the upper part 820. This can balance the competing considerations of ensuring the arrangement 800 is sufficiently compact to not interfere with the user, while ensuring that the arrangement 800 is sufficiently resilient and strong to withstand external impacts. Purely by way of example, the rim 818 may be 2 mm, the rim 820 may be 2.5 mm, and the clips 814 may be 1 mm.

Figure 11A:
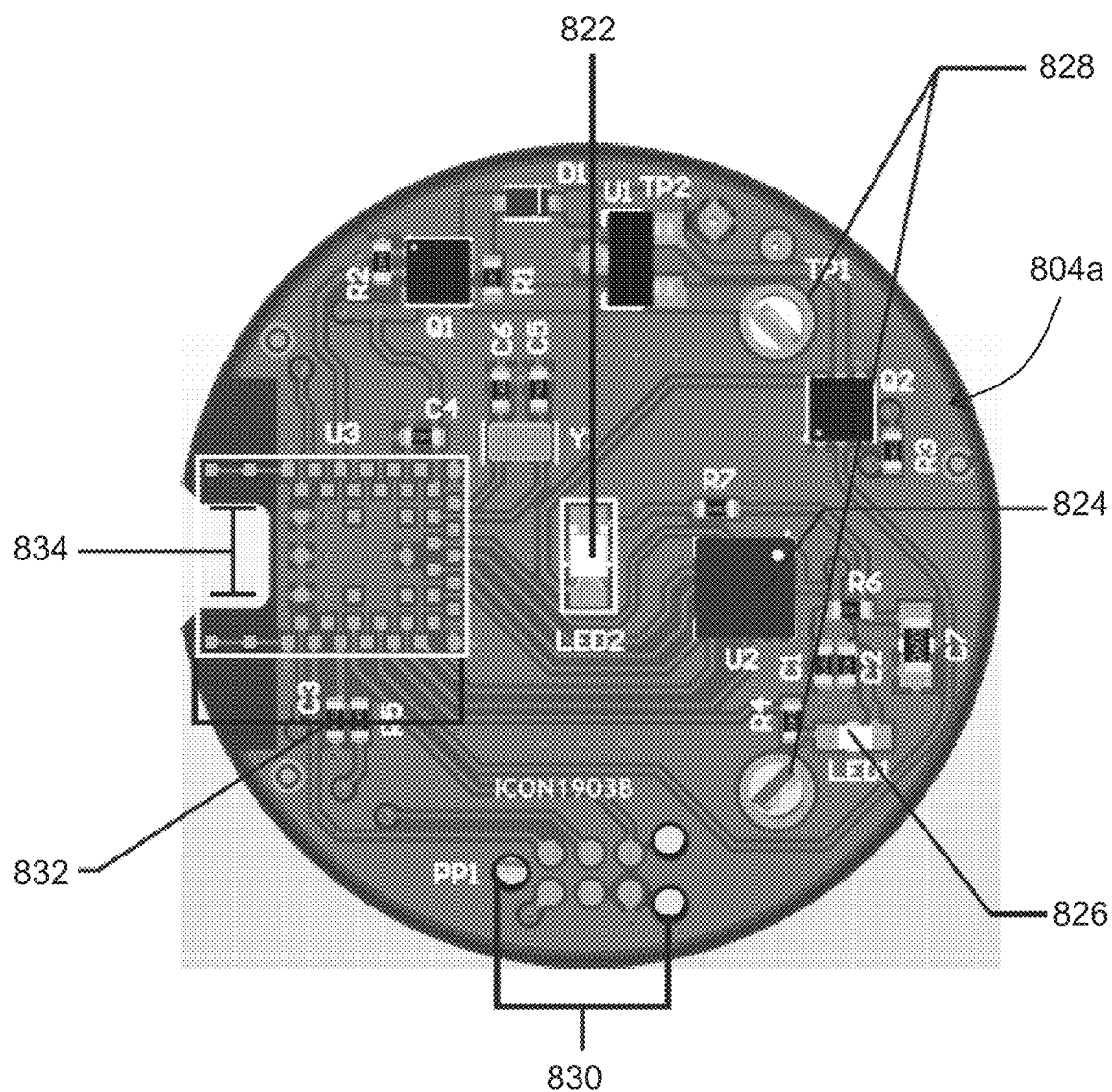
FIGS. 11(a) and 11(b) show front and rear sides, respectively, of a printed circuit board of the impact detection arrangement of FIG. 9.

FIG. 11(a) shows a front side 804a of the printed circuit board 804. In particular, a number of components that are part of the electrical circuit are arranged on the front side 804a. Specifically, the visual indicator in the form of an LED 822 (with high luminosity) which illuminates when the detected impact exceeds the threshold is on the front side 802a. Also, the sensor in the form of an accelerometer 824—measuring up to 100 G—is on the front side 804a. In the described example, the front side 804a also has an on/off LED 826 which illuminates when the arrangement 800 is switched on ready for use. Furthermore, FIG. 11a also indicates two holes 828 for a battery holder mounting, a six pin adapter 830 for uploading firmware, an outline of where a processor module 832 of the electrical circuit is to be positioned, and a gap 834 in the circuit board for an aerial to be positioned. The front side 804a of the printed circuit board 804 is arranged adjacent to the transparent screen 802c of the housing 802 so that the light produced by the LED may be viewed through the screen when activated.

Figure 11B:
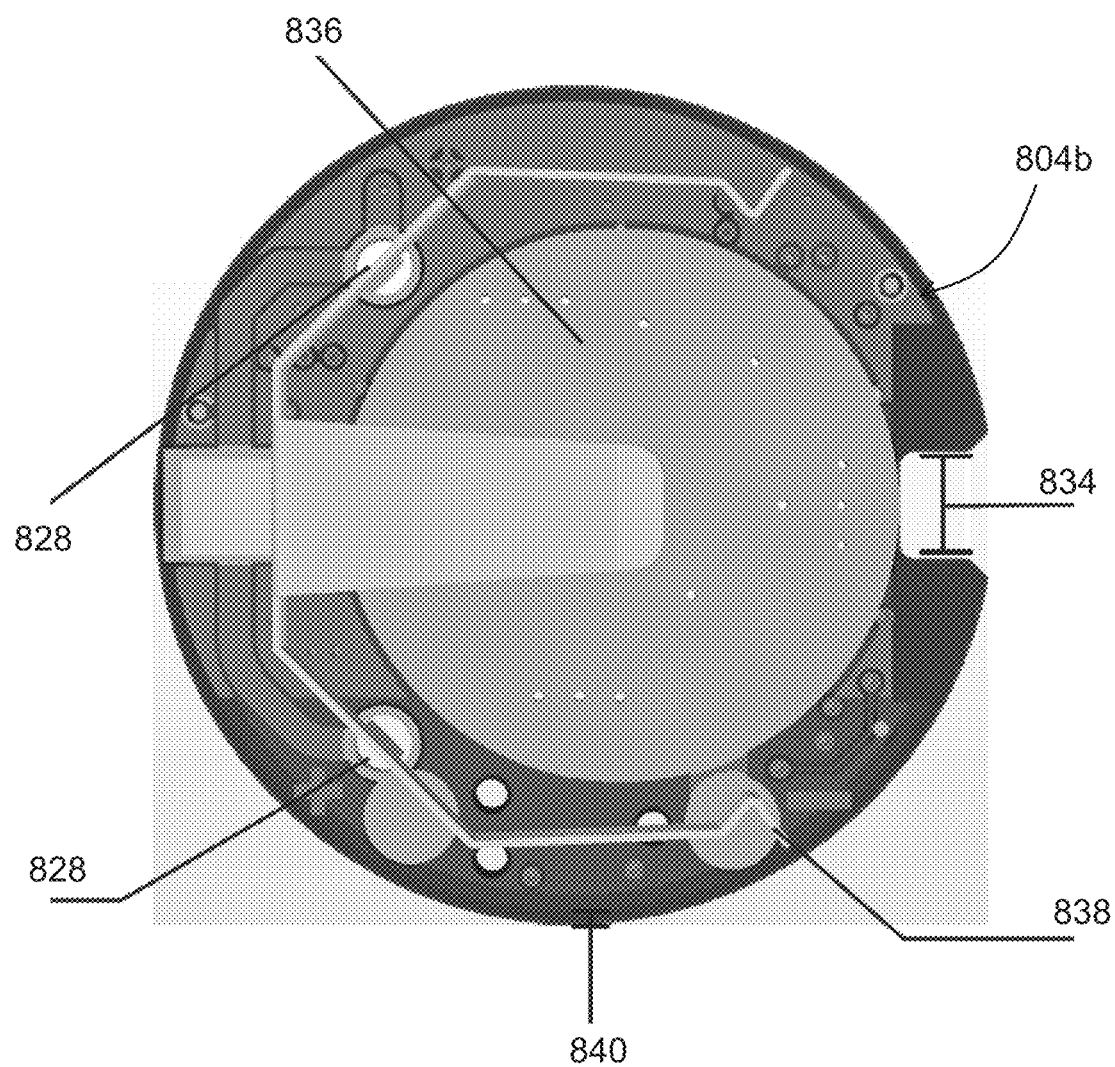

FIG. 11(b) shows a rear side 804b of the printed circuit board 804. In particular, the opposite sides of the two holes 828 for a battery holder mounting and the gap 834 for the aerial to be positioned are shown. A negative contact 836 for the coin cell battery 806 is arranged on the rear side 804b, as is a surface mount and two-pin mounted holder 838 for the battery 806. There is also a narrow space 840 around the outer perimeter of the rear side 804b for the substrate 804 to clip onto the casing 802.

As described, the arrangement 800 is designed so that the components of the electrical circuit are stacked on the top and bottom of a single printed circuit board to provide compactness and reduce the size of the arrangement 800. In particular, the arrangement 800 is constructed to be as small and compact as possible but provide enough power to usefully utilise the device and also protect the device from impacts in the choice of casing materials used, for instance. Regulations governing professional rugby stipulate that devices are to minimise discomfort to the wearer, and the described design of present device achieves this.

Figure 12:
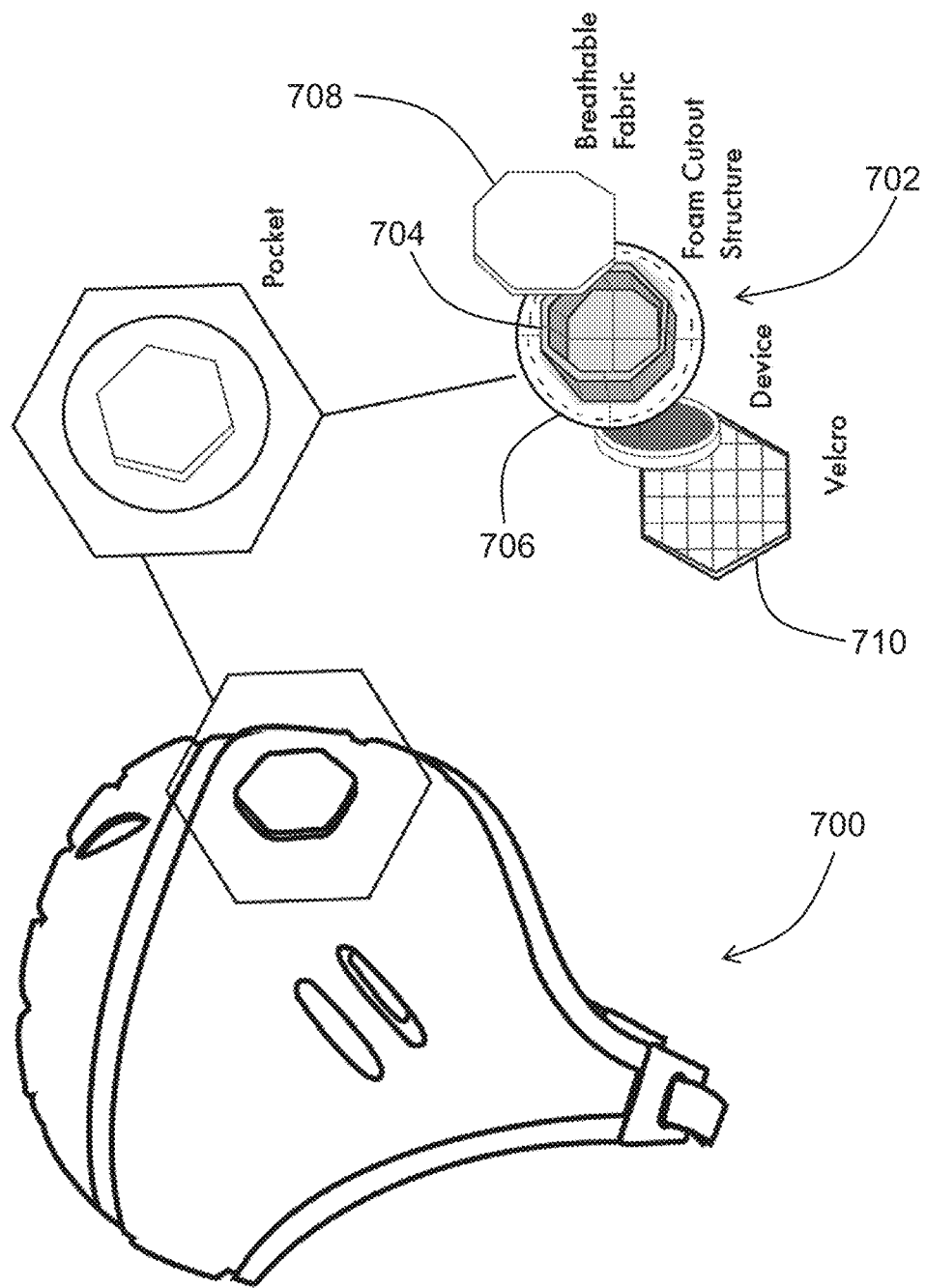
FIG. 12 shows a rugby head guard and a pocket insert for receiving the impact detection arrangement of FIG. 7 or FIG. 9.

FIG. 12 shows rugby apparatus including a rugby head guard 700 that is similar to the rugby head guard 70 in FIG. 6. The apparatus includes a pocket insert 702 for receiving the impact detection arrangement 80 of FIG. 7 or the impact detection arrangement 800 of FIG. 9. The head guard 700 has a hole through its entire thickness at its rear side. In the described example, the hole is located slightly away from a centre line of the guard 700 at its rear side.

The pocket 702 includes a protective surrounding portion 704 and a flange portion 706 extending from the surrounding portion 704. In this example, the pocket 702 is a foam cut-out structure. The surrounding portion 704 is sized to receive the impact detection arrangement 80, 800 to hold it securely in place. The pocket 702 is formed from a material that is less stiff—i.e. softer—than the housing of the impact detection arrangement 80, 800 in order to protect both: the arrangement 80, 800 from damage upon an impact being received; and, the user from the arrangement 80, 800 upon an impact being received. Note that the rugby head guard 700 is also formed from a relatively soft (or not hard) material, in particular less stiff than the housing of the impact detection arrangement 80, 800. In this example, the head guard 700 and the pocket 702 are formed from the same material, namely a foam material, to provide structural stability and to be compliant with regulations governing professional rugby. A depth of the surrounding portion 704 may be greater than a depth of the housing 802 of the impact detection arrangement to provide protection from impacts. The arrangement 800 is arranged in the pocket so that the transparent portion 802c of the housing 802 faces outwards away from the user's head so that the visual indicator may be viewed.

The pocket 702 is received into the hole of the guard 700 such that the flange portion 706 is at an inner side of the guard 700 and the surrounding portion 704 extends through the hole. The flange portion 704 is sewn to the guard 700 to secure the pocket 702 to the guard 700. Cutting out a small panel or hole allows the pocket 702 to slide into the hole created. The pocket 702 minimises any alteration to a direct impact that would occur anywhere else on the head while wearing the arrangement 80, 80.

The apparatus also includes an outer cover element 708 for covering the hole to the outside of the guard 700. In the described example, the element 708 is in the form of a breathable and stretchable fabric material, e.g. Spandex. The material 708 must be such that the visual indicator of the image detection arrangement 80, 800 can be viewed clearly through the material 708 from a sufficient distance, e.g. tens of metres. The element 708 is attached to the pocket 702 by sewing its edges to the flange portion 706. The outer cover element 708 provides an added layer of protection to the arrangement 80 800 from dirt and/or dust.

The apparatus further includes a removable inner cover element 710 for covering the hole at the inner side of the guard 700. In the described example, the element 710 is material approximately the diameter of the flange portion 706 of the pocket 702, and includes hook and loop means, e.g. Velcro®, for attaching and removing all or part of the element 710 to the flange portion 706. When the removable inner cover element 710 is attached it creates a tight seal and the impact detection arrangement 80, 800 is secured in the head guard 700. The inner cover element 710 can then be removed to allow access to the arrangement 80, 800 via the inner side of the head guard 700. This restricts access to the head guard 700 to when the guard 700 is not in use, i.e. when it is not being worn. Note that the outer and inner cover parts 708, 710 may also be referred to as being part of the pocket 702. The entire pocket (including cover elements) may be constructed as a single, entire insert for ease of manufacture.

The apparatus may further include a magnetic device or element (not shown) to switch the arrangement 80, 800 on/off and/or to reset the arrangement 80, 800. In particular, the electrical circuit of the arrangement 80, 800 includes an electrical switch for switching the impact detection arrangement 80, 800 between an operable state—i.e. on—and an inoperable state—i.e. off. The magnetic device operates the electrical switch by coming into close proximity with the electrical switch. Specifically, the electrical switch is arranged to change between the operable and inoperable states in response to the magnetic device being brought to within a threshold distance of the electrical switch. Hence, when the arrangement 80, 800 is in the head guard 700 the magnet can be tapped on the outside of the pocket to switch the arrangement 80, 800 on or off. By not having a switch than can be operated by a user's finger, for instance, the user cannot deactivate the arrangement 80, 800 during play, inadvertently or otherwise.

The magnet may be used to either switch the arrangement 80, 800 on/off or reset the arrangement, depending on how long the magnet is held in close proximity with to the arrangement. The electrical switch may be arranged to change between the operable and inoperable states in response to the magnetic device being maintained within the threshold distance for less than a threshold time, e.g. one second. The impact detection arrangement 80, 800 may be arranged to reset after the detected acceleration change exceeds the threshold acceleration change in response to the magnetic device being maintained within the threshold distance for greater than the threshold time. By reset, it may mean completely switching off the arrangement 80, 800, or simply turning off the visual indicator that has been activated.

Figure 13:
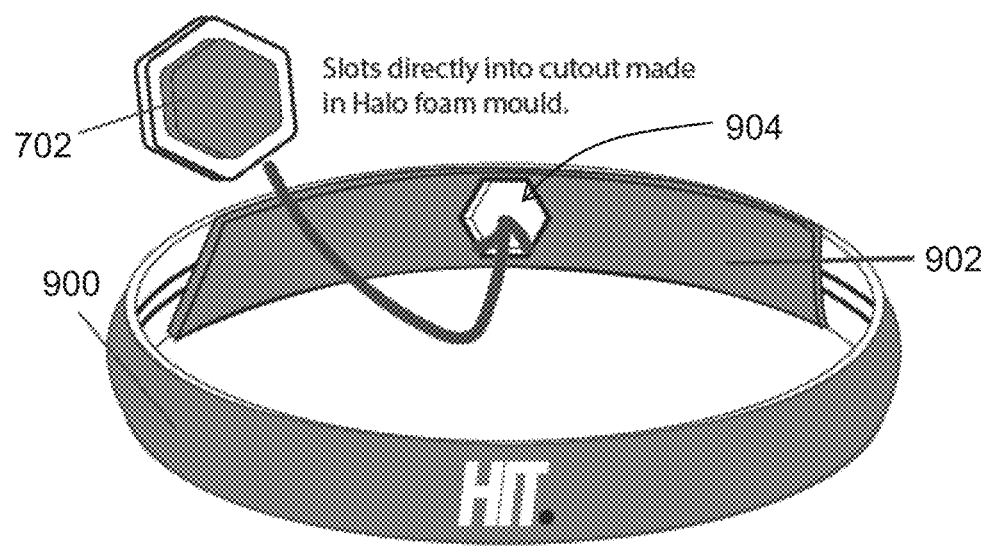
FIGS. 13(a) and 13(b) show front and rear views, respectively, of sports headwear fitted with the impact detection arrangement of FIG. 7 or FIG. 9; and, FIG. 14 shows the steps of a method undertaken by the impact detection arrangement of FIGS. 2, 7 and 9.
Figure 13:
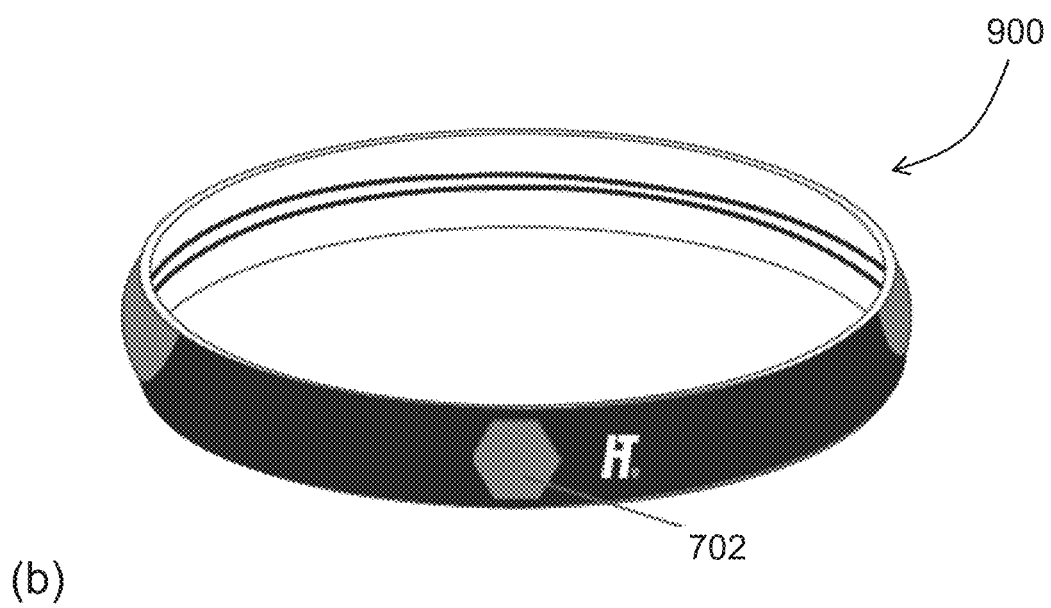
Figure 14:
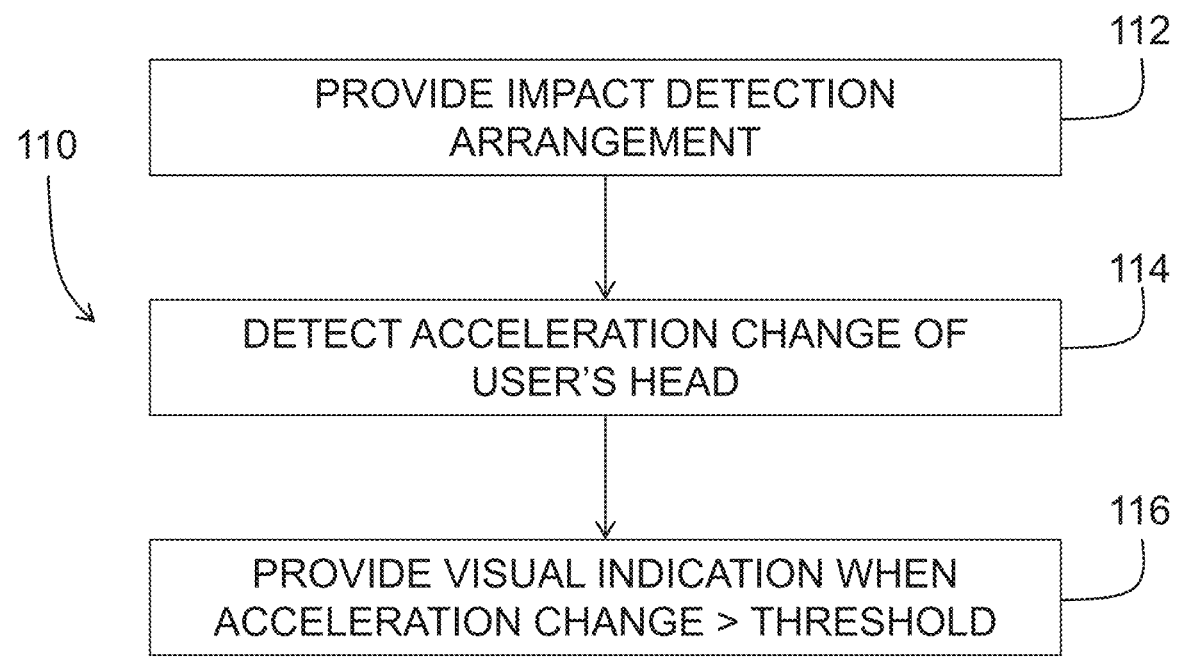

FIGS. 13(*a*) and 13(*b*) show front and rear views, respectively, of another example of sports headwear 900 or head gear with which the impact detection arrangement 80, 800 may be used. In particular, the sports headwear 900 is in the form of a head band or strap that extends around the user's head. The headwear 900 may be formed from a stretchable material—e.g. the same as the outer cover element mentioned above—so that it grips the user's head when worn. Such headwear may be used in a sport such as association football, in which a player repeatedly heading the ball, or clashing heads with another player, can pose a risk of injury or concussion. In this case, a layer of padding 902 is located at an inner, rear side of the headwear 900, extending around less than half the circumference of the headwear 900. This is of similar design to the rugby head guard cut-out above. A hole 904 is formed in the rear side of the headgear 900 (through the headgear 900 and padding 902)—so that the ball is less likely to come into contact with the arrangement 80, 800, for instance—and the pocket of the arrangement 80, 800, including the cover parts, is inserted and received into the hole 904. The pocket is attached to the headgear 900 in a similar manner to the rugby head guard 800 above. FIG. 14 summarises the steps of a method 110 performed by each of the arrangements 30, 80, 800 in the above-described examples in order to detect and report a high impact experienced by a user when the arrangements 30, 80, 800 are operational when a user is partaking in a sporting activity. In particular, prior to use the impact detection arrangement 30, 80, 800 is coupled to the head guard 10, 70, 700 by means of the pocket 16, 76, 702 and the user dons the head guard 10, 70, 700 in particular by the user's head being received into the main body 12, 72 of the head guard 10, 70, 700. The provision of the impact detection arrangement 30, 80, 800 for coupling to sports headwear, i.e. the head guard 10, 70, 700 to be worn by a user may be regarded as step 112 of the method 110.

With the head guard 10, 70, 700 secured to the user's head, the arrangement 30, 80, 800 is thereby also secured relative to the user's head. The sensor 38, 84 is therefore operable to detect changes in movement of the user's head. Specifically, the sensor 38, 84 is arranged to detect a change in acceleration of the user's head, also referred to as a g-force experienced by the user's head. That is, the accelerometer 38, 84 measures the directional change of the user's head and, in particular, the rate of this change. This detection or measurement of acceleration change may be regarded as step 114 in the method 110.

In the case of a shock, e.g. a collision, the g-force can be relatively large for a relatively short period. During sporting activity, such a shock can occur when a player is tackled or otherwise collides or impacts with another player. Note that a relatively large g-force may be experienced by a player's head even if the impact causing the large acceleration change is not received directly on the head. Along with a high impact to the head itself, a tackle where the direct impact is to the neck or other part of the body may also cause a large acceleration change to the head. When a player's head experiences a large acceleration change caused by a high impact, the player is at risk of concussion and needs to be checked by medical personnel before being allowed to continue playing, in particular to guard against second impact syndrome. It is therefore imperative that high g-forces experienced by the player's head are detected and communicated.

In order to achieve this, at step 116 the visual indicator in the form of LEDs 44, 94 are arranged to activate, i.e. to light up, when the acceleration change or g-force detected by the sensor 38, 84 rises above a threshold value. This provides a visual indication or warning to other people in the vicinity of the player, e.g. other players, referees, coaching staff, that the player has received a high impact and should be checked for signs of concussion before being permitted to continue playing. Specifically, the sensor 38, 84 is connected to, and calibrated by, a microprocessor of the circuit board 36, 82 that recognises when the received or detected impact exceeds the threshold change value. Upon exceeding the threshold, a switch of the circuit board 36, 82 is arranged to open to cause the visual indicator to activate, i.e. to cause the LEDs 44, 94 to illuminate.

In the described example, the LEDs 44, 94 remain on upon detection of the above-threshold g-force until the arrangement 30, 80, 800 has been reset, e.g. until the player has been checked. In different examples, the LEDs may remain on for a predetermined amount of time upon detection of the above-threshold g-force.

In the described example, the threshold change value is a predetermined threshold value. For instance, an appropriate threshold for an adult player may be approximately 60 G, where G is a measure of the g-force change, i.e. a measure of acceleration change relative to free fall. It will be understood that this particular value if for illustration only, and any appropriate threshold value may be used.

In some examples, the threshold may be user-adjustable to be suitable for a particular user. For example, the appropriate threshold value for a child player may be less than for an adult player. The threshold value may therefore by adjusted and set in dependence on the particular user. In addition to, or alternatively to, the threshold being varied based on the age of the user, the threshold may also be varied in dependence on the level of sporting activity at which the player is participating. In rugby for example, the threshold may be varied depending on whether the player or user is participating in professional rugby or amateur rugby. For instance, the threshold value may be lower for amateur level than for professional level.

The wireless radio transmitter 42, 88 may be used to send impact data collected by the microchip 36, 82 from the arrangement 30, 80 to a mobile device, e.g. a mobile smartphone or tablet device. In particular, the impact data received by the mobile device may be recorded and monitored, for example via a specific application, so that a user of the mobile device can track and monitor the received impacts to make a determination as to whether medical attention is needed or to provide specific medical advice based on the received impact data. The signals may be sent in real time so that users of the mobile device on the sidelines may be provided with live updates. Note that all of the detected impact data, and not necessarily just data above the threshold value, may be sent to the mobile device. The transmitted signals including the impact data may be in the form of, for example, Bluetooth® signals or radio-frequency identification (RFID) signals. For instance, the signals may be in the form of high-frequency sound waves as they may be clearer or have less disruption than other types of signals.

It will be appreciated that various changes and modifications may be made to the above-described embodiments and examples without departing from the scope of the present disclosure as defined in the accompanying claims.

In the above-described examples, the impact detection arrangement is coupled to a rugby head guard and used to detect impacts to a rugby player wearing the head guard when playing rugby. In different examples, however, the impact detection arrangement may be used to detect impacts received by a person taking part in a different sport. In particular, the impact detection arrangement may be coupled to sports headgear other than a rugby head guard. Examples of other sports in which the impact detection arrangement may be used include, but are not limited to, cycling and association football. The sports headgear to which the impact detection arrangement is coupled may be protective headgear, a helmet, used in these or other sports, or another form of sports headgear.

In the above-described examples, the impact detection arrangement has a single threshold g-force change value where a single impact above said threshold is considered to provide a concussion risk and therefore causes the visual indicator to be activated. However, when a player receives a number (greater than one) of impacts over a certain level (but less than the threshold) then the player may similarly be at risk of concussion. In different examples, therefore, there is a second threshold value less than the (first) threshold value, whereby the visual indicator is arranged to activate when the detected g-force change rises above the second threshold value a predetermined number of times greater than one.

In the above-described examples, one or more LEDs are used to provide visual indication of a high impact having occurred. In different examples, however, a different form of visual indicator may be used. For instance, different kinds of lights other than LEDs may be used. Also, the visual indicator need to not be an electronic visual indicator, e.g. light indicator, and could instead, for example, be in the form of a dye in a transparent container, where the dye is released (and can be seen) when the detected g-force is above the threshold.

In the above-described examples, the impact detection arrangement is coupled to the head guard by means of a pocket associated with the head guard, e.g. the pocket may be sewn onto the head guard, during manufacture or otherwise, or the pocket may be integrally formed with the head guard. In different examples, the impact detection arrangement may be coupled to the head guard without the need of a pocket to receive the head guard. In the case of rugby specifically, the impact detection arrangement may be attached or connected directly to the rugby head guard. In particular, the arrangement may be attached to an internal plate positioned at an inner side of the head guard. The plate may have connection points or features, such as sprockets, that extend or fit through eyelets holding lacing of the head guard, and may in turn connect to corresponding connection points on the arrangement, so as to secure the arrangement to the head guard, and therefore secure the arrangement relative to the user's head.

In the above-described examples, the visual indicator (in the form of LEDs) is either in an 'off-state', i.e. when the received impacts have not exceeded the threshold, or an 'on-state', i.e. when a received impact exceeds the threshold. In different examples, however, the visual indicator may activate (light up) in a gradual manner. For instance, the level of luminosity of the visual indicator may indicate the number of impacts over a certain threshold that the player has received, where a greater luminosity means a greater number of high impacts.

Although the arrangements in FIGS. 7 and 9 are shown as being generally circular, in different examples an arrangement may generally have rounded edges without necessarily being circular, while still maintaining the required compactness and no sharp edges (which could cause injury or damage).

Further examples of the present disclosure are given in the following numbered statements.

1. Impact detection arrangement for coupling to a rugby head guard to be worn by a user, the arrangement comprising: a sensor configured to detect an indication of an acceleration change experienced by the user's head when the rugby head guard is being worn; and, a visual indicator configured to provide a visual indication when the detected acceleration change exceeds a threshold.

2. Impact detection arrangement according to statement 1, wherein the sensor comprises an accelerometer.

3. Impact detection arrangement according to any previous statement, wherein the visual indicator comprises a light indicator.

4. Impact detection arrangement according to statement 3, wherein the light indicator comprises one or more LEDs.

5. Impact detection arrangement according to any previous statement, wherein the sensor is positioned on a first substrate and the visual indicator is positioned on a second substrate separate from the first substrate.

6. Impact detection arrangement according to any previous statement, wherein the visual indicator is arranged atop the sensor.

7. Impact detection arrangement according to any previous statement, wherein the threshold is user-adjustable.

8. Impact detection arrangement according to any previous statement, wherein the threshold is a first threshold greater than a second threshold, and wherein the visual indicator is configured to provide the visual indication when the detected acceleration change exceeds the second threshold a predetermined number of times greater than one.

9. Impact detection arrangement according to any previous statement, the arrangement comprising a housing arranged to house the sensor and the visual indicator.

10. Impact detection arrangement according to statement 9, wherein the housing is formed from a flexible material.

11. Impact detection arrangement according to statement 9 or statement 10, wherein at least part of the housing is formed from a transparent material.

12. Impact detection arrangement according to any of statements 9 to 11, wherein the housing is formed from thermoplastic polyurethane.

13. Impact detection arrangement according to any of statements 9 to 12, wherein the housing is generally elongate.

14. Impact detection arrangement according to any of statements 9 to 13, wherein the housing is shaped to conform to a curvature of the user's head.

15. Impact detection arrangement according to any of statements 9 to 14, wherein the housing comprises a first housing part arranged to house the sensor and a second housing part configured to house the visual indicator.

16. Impact detection arrangement according to statement 15, wherein the arrangement comprises a locking mechanism arranged to connect the first and second housing parts together.

17. Impact detection arrangement according to any of statements 9 to 12, wherein the housing is generally circular.

18. Impact detection arrangement according to any previous statement, wherein the sensor is configured to receive data indicative of the acceleration change experienced by the user's head, and wherein the arrangement comprises a wireless transmitter configured to transmit the received acceleration data off-board the arrangement, optionally wherein the acceleration data is transmitted to a mobile device.

19. Sports headwear, comprising: a main body arranged to receive a user's head; and, a pocket coupled to the main body and arranged to receive the impact detection arrangement of any previous claim, so as to couple the impact detection arrangement to the sports headwear.

20. Sports headwear according to statement 19, wherein the pocket is positioned at rear side of the sports headwear, optionally wherein the pocket is positioned at a central part of the main body of the head guard.

21. Sports headwear according to statement 19 or statement 20, wherein the pocket is in the form of a fabric sleeve.

22. Sports headwear according to any of statement 19 to 21, wherein the pocket is integrally formed with the main body.

23. Sports headwear according to any of statement 19 to 22, wherein the sports headwear is a rugby head guard.

24. Apparatus for sports impact detection, the apparatus comprising: the impact detection arrangement of any of statements 1 to 18; and, the sports headwear of any of statement 19 to 23, wherein the sports headwear is arranged to be worn on a user's head and the impact detection arrangement is arranged to be coupled to the sports headwear to detect acceleration change experienced by the user's head upon the user receiving an impact.

25. An impact detection method, comprising: providing an impact detection arrangement for coupling to sports headwear to be worn by a user, the arrangement having a sensor and a visual indicator; detecting, using the sensor, an indication of an acceleration change experienced by the user's head when the sports headwear is being worn; and, providing a visual indication using the visual indicator when the detected acceleration change exceeds a threshold.

The invention claimed is:

1. A head protective apparatus, comprising:
a head guard arranged to receive a user's head;
a polygonal pocket configured to affix into said head guard by way of a hole formed in the head guard; and,
an impact detection arrangement configured to be receivable into the pocket;
the impact detection arrangement comprising:
a sensor configured to detect an indication of an acceleration change experienced by the user's head when the head guard is being worn;
a visual indicator configured to provide a visual indication when the detected acceleration change exceeds a threshold; and,
a housing arranged to house the sensor and the visual indicator;
wherein a part of the housing adjacent to the visual indicator is formed from a transparent material, and wherein the pocket is formed from a material having a lower stiffness than a stiffness of the housing.

2. The head protective apparatus according to claim 1, wherein the pocket is formed from the same material as the head guard.

3. The head protective apparatus according to claim 1, wherein the pocket is formed from a foam material.

4. The head protective apparatus according to claim 1, wherein the pocket includes a protective surrounding portion defining an aperture sized to receive and secure the impact detection arrangement therein.

5. The head protective apparatus according to claim 4, wherein the pocket includes a flange portion extending from the protective surrounding portion, and wherein the flange portion is attached to a surface of the head guard.

6. The head protective apparatus according to claim 1, wherein the pocket includes a protective surrounding portion defining an aperture sized to receive and secure the impact detection arrangement therein; and, wherein a depth of the surrounding portion is greater than a depth of the housing of the impact detection arrangement.

7. The head protective apparatus according to claim 1, wherein the pocket is attached to the head guard by sewing.

8. The head protective apparatus according to claim 1, wherein the housing is formed from a flexible material.

9. The head protective apparatus according to claim 1, wherein the housing is formed from thermoplastic polyurethane.

10. The head protective apparatus according to claim 1, wherein the housing has rounded edges, optionally wherein the housing is generally circular.

11. The head protective apparatus according to claim 1, wherein the housing is generally planar.

12. The head protective apparatus according to claim 1, wherein the housing includes at least two component parts attached together by snap fitting to house the sensor and the visual indicator.

13. The head protective apparatus according to claim 1, wherein the impact detection arrangement includes only a single printed circuit board, and wherein the sensor and the visual indicator are arranged on the single printed circuit board.

14. The head protective apparatus according to claim 1, wherein the apparatus comprises an outer cover element for attaching to the pocket and for covering an outer part of the hole of the head guard, wherein the outer cover element is formed from a material through which the visual indicator is visible, and wherein the outer cover element is formed from a material having a stiffness less than a stiffness of the housing of the impact detection arrangement.

15. The head protective apparatus according to claim 14, wherein the outer cover element is formed from a fabric material, optionally a stretchable material.

16. The head protective apparatus according to claim 1, wherein the apparatus comprises a removable inner cover element for attaching to the pocket and for selectively covering or revealing an inner part of the hole of the head guard.

17. A head protective apparatus, comprising:
a head guard arranged to receive a user's head;
a polygonal pocket configured to affix into said head guard by way of a hole formed in the head guard; and,
an impact detection arrangement configured to be receivable into the pocket;
the impact detection arrangement comprising:
a sensor configured to detect an indication of an acceleration change experienced by the user's head when the head guard is being worn; and,
a visual indicator configured to provide a visual indication when the detected acceleration change exceeds a threshold,
wherein the impact detection arrangement further comprises a housing arranged to house the sensor and the visual indicator;
wherein the pocket is formed from a material having a lower stiffness than a stiffness of the housing of the impact detection arrangement;
wherein the housing includes at least two component parts attached together by snap fitting to house the sensor and visual indicator.

18. A head protective apparatus, comprising:
a head guard arranged to receive a user's head;
a polygonal pocket configured to affix into said head guard by way of a hole formed in the head guard; and,
an impact detection arrangement configured to be receivable into the pocket;
the impact detection arrangement comprising:
a sensor configured to detect an indication of an acceleration change experienced by the user's head when the head guard is being worn; and,
a visual indicator configured to provide a visual indication when the detected acceleration change exceeds a threshold;
wherein the head protective apparatus comprises a removable inner cover element for attaching to the pocket and for selectively covering or revealing an inner part of the hole of the head guard.

\* \* \* \* \*